(12) United States Patent
Saunin et al.

(10) Patent No.: US 9,910,066 B2
(45) Date of Patent: Mar. 6, 2018

(54) SYSTEMS AND METHODS FOR NON-DESTRUCTIVE SURFACE CHEMICAL ANALYSIS OF SAMPLES

(71) Applicant: AIST-NT, Inc., Novato, CA (US)

(72) Inventors: Sergey A. Saunin, Novato, CA (US); Andrey V. Krayev, Novato, CA (US); Vladimir V. Zhishimontov, Santa Rosa, CA (US); Vasily V. Gavrilyuk, Moscow (RU); Leonid N. Grigorov, Novato, CA (US); Alexey V. Belyaev, Moscow district (RU); Dmitry A. Evplov, Moscow district (RU)

(73) Assignee: HORIBA INSTRUMENTS, INC., Irvine, CA (US)

( * ) Notice: Subject to any disclaimer, the term of this patent is extended or adjusted under 35 U.S.C. 154(b) by 0 days.

(21) Appl. No.: 14/717,576

(22) Filed: May 20, 2015

(65) Prior Publication Data
US 2015/0338439 A1  Nov. 26, 2015

Related U.S. Application Data

(60) Provisional application No. 62/002,877, filed on May 25, 2014.

(51) Int. Cl.
*G01Q 60/18* (2010.01)
*G01N 21/65* (2006.01)
(Continued)

(52) U.S. Cl.
CPC ............. *G01Q 60/18* (2013.01); *G01N 21/65* (2013.01); *G01Q 30/02* (2013.01); *G01Q 60/20* (2013.01); *G01Q 60/34* (2013.01)

(58) Field of Classification Search
CPC ........ G01Q 10/00; G01Q 10/02; G01Q 10/04; G01Q 20/00; G01Q 20/02; G01Q 30/00;
(Continued)

(56) References Cited

U.S. PATENT DOCUMENTS 6,313,461 B1 * 11/2001 McClelland ........... B82Y 15/00
250/305
2003/0182993 A1 * 10/2003 Hantschel .............. B82Y 35/00
73/105

(Continued)

OTHER PUBLICATIONS

Bailo, Elena; Tip-Enhanced Raman Spectroscopy of Single RNA Strands: Towards a Novel Direct-Sequencing Method, 2008 Wiley-VCH Verlag GmbH & Co, Angew.Chem,Int.Ed 2008, 47, 1658-1661.

(Continued)

*Primary Examiner* — Jason McCormack
(74) *Attorney, Agent, or Firm* — D. Benjamin Borson; Borson Law Group, PC

(57) ABSTRACT

Aspects of the present invention include systems, devices, and methods of surface chemical analysis of solid samples, and particularly it relates to methods of chemical analysis of molecular compounds located either on or within thin surface layer of solid samples. Even more particularly, aspects of the present invention relate to systems, devices, and non-destructive methods combining both high sensitivity and high spatial resolution of analysis of chemical compounds located or distributed on the surface of solid samples with obtaining most important information regarding vibration spectra of atoms and molecular groups contained in thin surface layer of solid samples. These objectives are realized by implementation of computer-assisted systems that carefully regulate the motion of, and force applied to probes of atomic force microscopes.

13 Claims, 8 Drawing Sheets

(51) Int. Cl.
*G01Q 30/02* (2010.01)
*G01Q 60/20* (2010.01)
*G01Q 60/34* (2010.01)

(58) Field of Classification Search
CPC ...... G01Q 30/02; G01Q 30/025; G01Q 60/00; G01Q 60/02; G01Q 60/34
USPC ............. 850/1, 2, 3, 6, 8, 22, 33, 35, 38, 52
See application file for complete search history.

(56) References Cited

U.S. PATENT DOCUMENTS

| | | | | |
|---|---|---|---|---|
| 2004/0089816 | A1* | 5/2004 | Quake | B82Y 10/00 250/458.1 |
| 2004/0173378 | A1* | 9/2004 | Zhou | B82Y 10/00 174/260 |
| 2008/0308718 | A1* | 12/2008 | Kollin | B82Y 35/00 250/252.1 |
| 2009/0249522 | A1* | 10/2009 | Xu | G01Q 60/40 850/41 |
| 2010/0218287 | A1* | 8/2010 | Nakata | G01Q 70/12 850/6 |

OTHER PUBLICATIONS

Hayazawa, Norihiko, "Highly reproducible tip-enhanced Raman scattering using an oxidized and metallized silicon cantilever tip as a tool for everyone"; J.Raman Spectroxc 2012 43, 1177-1182.

S. Hoffman, "Sputter depth profiling for thin-film analysis"; The Royal Society Publishing, vol. 362, No. 1814, pp. 55-75.

A. Benninghoven, "Analysis of submonoloayers on silver by negative secondary ion emission"; phys.stat.sol. 34, K169 (1969).

R. Eckert, "X-Ray fluorescence in the SEM—Advantages in material analysis"; SCANNING vol. 8, 232-238 (1986) FACM, Inc.

Chang, Chuan C., "Auger electron spectroscopy"; Surface Science 25 (1971) 53-79, North-Holland Publishing Co.

* cited by examiner

SYSTEMS AND METHODS FOR NON-DESTRUCTIVE SURFACE CHEMICAL ANALYSIS OF SAMPLES

CLAIM OF PRIORITY

This application claims priority to U.S. Provisional Patent Application No. 62/002,877 filed 25 May 2014 entitled "Systems and Methods for Non-Destructive Surface Chemical Analysis of Samples," Inventors: Sergey A. Saunin, Andrey V. Krayev, Vladimir V. Zhizhimontov, Vasily V. Gavrilyuk, Leonid N. Grigorov, Alexey V. Belyaev, and Dmitry Evplov. The contents of the above-identified application is herein incorporated fully by reference.

FIELD OF THE INVENTION

Aspects of the present invention relate to systems and methods of surface chemical analysis of solid samples, and particularly it relates to methods of chemical analysis of molecular compounds located either on or within thin surface layer of solid samples. Even more particularly, aspects of the present invention relate to systems and non-destructive methods combining both high sensitivity and high spatial resolution of analysis of chemical compounds located or distributed on the surface of solid samples with obtaining most important information regarding vibration spectra of atoms and molecular groups contained in thin surface layer of solid samples.

BACKGROUND

Identifying and quantitating molecular structures on surfaces is an important aspect of manufacturing of many products, including computer wafers. In many situations, manufacture of such wafers requires numerous steps of chemical mechanical polishing, deposition of metal layers, deposition of dielectric materials, and deposition and removal of masking materials. Manufacturing steps have become to production of high-speed, small computing devices, such as main-frame computers, desk-top computers, laptop computers, hand-held computers, cellular telephones, tablet computers, digital watches, sensors, and numerous other modern devices. As the size of computer chips continues to decrease in size, and the density of elements, such as switches, diodes, capacitive elements, resistive elements and other features on chips decreases, measurement of the surface features of wafers and chips during manufacturing is becoming increasingly important to production of high quality products.

Other products including machined parts for sophisticated devices are also improving in quality and accuracy. However, during manufacture of such products, environmental and manufacturing conditions may result in deposition of unwanted materials on the surfaces of such products and the parts that make up the products. As the accuracy and consistency of manufacture of many products increases, detection of contaminants is becoming more important.

SUMMARY

We have identified a new problem in the field, namely how to develop systems, devices, and methods that provide advantages of Tip Enhanced Raman Scattering ("TERS") phenomena and at the same time, provide increased sensitivity, increased spatial resolution and avoidance of damage to the scanned surface of probes used for TERS scanning.

Therefore, one aim of present invention is to develop such improved method of surface chemical analysis of solid samples which is non-destructive method and simultaneously possesses all previously known advantages of TERS phenomena in regard of excellent sensitivity and spatial resolution.

Another aim of present invention is to remove known disadvantages of prior art method in which scanning probe microscope is used as a part of analytical equipment.

One more aim of the present invention is to provide excellent reproducibility of results of chemical analysis if given sample is analyzed repeatedly as many times as necessary or desirable.

More particularly an aim of present invention is to develop such systems, devices, and methods in which neither a sample nor a tip of the needle used to participate in TERS phenomena can be damaged while scanning the surface of the sample.

A further aim of present invention is to develop such adjustable method in which highest possible sensitivity of TERS phenomena can be achieved in accordance with each particular combination of the nature of the sample and chosen type of the probe to provide either TERS effect or any other optical effect (for example, laser-induced fluorescence) caused by laser illumination of sharp tip of scanning probe microscope.

Typical materials for the probe and its sharp tip include: silicon, silicon oxide, and such metals as silver and gold. In some relatively recently developed cases the tip can be made of small diamond crystal. In the case of non-metallic probes suitable for TERS the tip must be covered with thin metallic layer (silver or gold) made by vacuum sputtering. This list shows that main mechanical properties of the tip (strength and elasticity) are in typical range of solids.

It can be appreciated that probes having increased elasticity can help reduce damage to the surface to be analyzed. Instead of breaking the surface or itself, if a probe is sufficiently flexible to bend, it can move over the surface without causing damage. However, if the probe tip is too elastic, then it may not be sufficiently rigid to provide the degree of tight contact with the surface to produce a desirably high degree of TERS performance.

In order to achieve all these aims the method of present invention combines three following general features:

I. The method of present invention fully removes a combination of two subsequent steps of prior art method causing damages to samples and probes, namely the combination of the step #2 with the step #3 of prior art described later. This combination corresponds to the only regime of prior art operation in which non-interrupted too tight direct contact (either electric or mechanical one) between the probe and the surface of solid sample is simultaneously combined with continuous movement of said probe along the surface.

II. A preliminary step of the method of present invention provides:

Step (a): Provide a device comprising a scanning probe microscope (SPM) operably linked with an optical spectrometer so that said device is capable of performing one or more of the following operations:
  (i) programmable switching between at least two different regimes of SPM operation while scanning of sample's surface;
  (ii) relocating either the sample or a probe of said microscope for changing programmatically position of said probe relatively said sample in any of three dimensions in each of said two regimes, (iii) illuminating a sharp tip of said probe with focused laser beam, (iv) collecting a light emitted from proximity of said sharp tip for spectrometric analysis provided by said optical spectrometer; and (v) memorizing both current coordinates of the probe and results of said spectrometric analysis related to said current coordinates.

III. Non-destructive methods of the present invention are based on periodic switching between at least two different regimes in each particular point of surface chemical analysis wherein a specific aim of the first of said two regimes is safe preliminary observation of relief parameters of a chosen point, and a specific aim of the second regime is safe obtaining of chemical information from that point. That is why methods of present invention provide such new sequences of main steps that surface chemical analysis is to be interrupted periodically in correlation with periodic switching between two different regimes of the scanning probe microscope, said switching resulting in fully modified trajectory of point-to-point relocation of the probe while scanning, which corresponds in general to periodic hopping from one local surface area of the sample to a next one. A specificity of such invented hopping of said probe is that in each local surface area the probe is to be delayed in a position of appropriately tight contact with sample's surface, whereas said chemical analysis is performed at the time of said delaying which is shorter than 0.2 s by the order of magnitude and either longer or equal 0.0001 s. In order to achieve specific advantages of the feature III mentioned herein, methods of present invention comprise one or more of the following main steps repeated periodically.

Step (b): Initiate a first regime of said SPM, for example so-called intermittent contact regime in which controllable relocation of the probe along sample's surface is safe, whereas damage of both the tip and the sample are reduced by keeping at least a predetermined minimum safe distance $D_{safe}$ between said sharp tip and a surface of the sample.

Step (c): Select programmatically a next desirable point of chemical analysis. In some embodiments of the invention this selecting comprises moving either the probe or the sample in X-Y plane, which is substantially parallel to sample's surface, in order to locate said sharp tip of the probe over said next desired point of the sample so that this locating takes desirably not longer than predetermined time interval $\tau_1$. In other embodiments said moving may be skipped at least one time if chemical analysis is desired to be repeated in the same point of sample's surface. Also in some embodiments this step (c) may comprise memorizing numeric value of $Z_0$-position of the probe relatively either the sample or stable base of SPM, said $Z_0$-position corresponding to said first regime and established in either step (c) or step (b) to provide at least said minimum distance $D_{safe}$ between said sharp tip and the surface of the sample in proximity of each said desirable point;

Step (d): Switching SPM from said first regime to a second regime by changing at least one setting parameter of SPM operation. In some embodiments of present invention said change of at least one setting parameter may relate to change of predetermined value of feedback signal. In other embodiments said change of setting parameter may relate to a system operating with signals of at least one coordinate sensor associated with Z-position of the probe when feedback system of SPM is disabled temporarily. In this case memorizing $Z_0$-position established in either step (c) or step (b) is required as well.

Step (e): Changing Z-position of the probe relatively the sample using SPM operation in said second regime so that a new Z-position is more appropriate for chemical analysis of the light emitted from proximity of said sharp tip than said $Z_0$-position. Said new Z-position established accordingly to said second regime of step (d) satisfies following programmatically predetermined conditions:

(i) said new Z-position=$\Delta Z+Z_0$-position, wherein $\Delta Z$ is a non-zero separately determined parameter, and (ii) said new Z-position results in no damages to both the sharp tip and the sample when a new distance $D_{record}$ between said sharp tip and the surface of the sample is kept for programmatically predetermined limited time interval $\tau_2$. In some cases depending on both the nature of the sample and material of the tip, said new Z-position may correspond to a decreased distance between the tip and sample's surface which results in their tight contact. In other, relatively rare cases, a new Z-position may correspond to an increased distance between these two elements;

Step (f): Illuminate said sharp tip of said probe with a focused laser beam;

Step (g): Collecting the light emitted from proximity of said sharp tip for further directing a collected light onto an entrance of said optical spectrometer;

Step (h): Initiating data recording, said data obtained from spectrometric analysis of said collected light by said optical spectrometer, said recording continuing for a predetermined time interval which doesn't exceed programmatically predetermined limited time interval $\tau_2$;

Step (i): Interrupting data recording, said interrupting performed on or before of the end of said time interval $\tau_2$ in which the probe makes contact with the sample tightly in most embodiments;

Step (j): Store in memory both data record accumulated while step (h) and coordinates of the probe relatively the sample corresponding to current point of analysis. The data obtained contain information related to chemical compounds located in said selected point on the surface;

Step (k): Terminate the method if both said selected point of chemical analysis is the last one and all programmatically desirable steps (f-j) of data accumulation are over in this last point. Otherwise return to step (b) in which SPM will be switched again to the first regime in order to:

(i) terminate the second regime of SPM operation and relocate the probe safely to next desired point of the surface of the sample, and (ii) repeat the sequence of steps (c-k) for surface chemical analysis in next desired point.

In the last case the step (k) provides cyclic repeating of the method of present invention and means to return to safe $Z_0$-position of the probe relatively the sample which decreases the likelihood of damage while traveling of the probe along main XY surface plane of the sample.

General steps of invented method listed above may be performed differently in wide variety of different embodiments of the invention. Accordingly to these variations certain optional technical details of a device represented in the step (a) can vary as well in order to provide as high sensitivity and spatial resolution as possible. For example, in some embodiments of the invention the direction of focused laser beam participating in step (f) may differ from general direction of the light collected in step (g). In other embodiments of the invention it may be useful that at least part of a path of laser beam participating in step (f) is directed coaxially with general axis of the light collected in step (g). As another example, in other embodiments it may be useful that, in framework of the same scope of the invention, the system of the device performing said illumination of said sharp tip is capable of periodic interrupting the illumination, said interrupting synchronized with said switching regimes of SPM operation. There are also other optional technical improvements of the device represented in step (a) which may logically follow from specific peculiarities of different steps listed above.

BRIEF DESCRIPTION OF THE DRAWINGS

This invention is described with reference to specific embodiments thereof. Other features of the systems and methods can be understood with reference to the figures, in which.

DETAILED DESCRIPTION

Definitions

Figure 1:
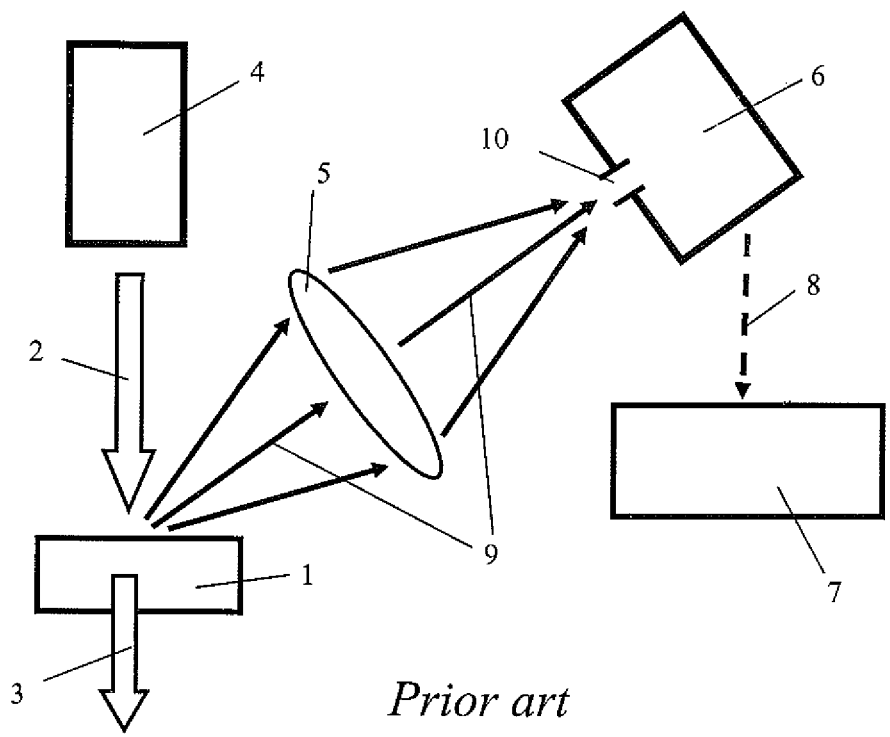
FIG. 1 depicts a general block-diagram of equipment used for traditional Raman spectroscopy.

The terms following, unless defined specifically elsewhere in this application have the following meanings.

The term "X-Y" means a plane defined by two axes, and X axis and a Y axis, being generally at right angles with respect to each other.

The term "Z" means an axis perpendicular to said X-Y plane.

The term "ΔZ" means a difference between one value on the Z axis and a second value on the Z axis.

The term "comprises," "comprising" and "having" means "includes but not limited to" the stated terms.

The term "consists of," "consisting of," and like terms means "includes and does not include other than the stated terms".

The terms "a," and "an" mean the indefinite article, and means "one or more."

The terms "the" and "said" mean the definite article and means only the (or those) referred to previously.

The term "TERS" means Tip Enhanced Raman Spectroscopy.

The term "SERS" means Surface Enhanced Raman Spectroscopy.

The term "SPM" means Scanning Probe Microscope.

The term "AMF" means Atomic Force Microscope.

The term "XPS" means X-ray photoelectron spectroscopy.

The terms "tip," "sharp tip," "probe tip," and "hard tip" mean the terminal portion of a probe used for TERS.

The terms "probe" and "needle" mean a portion of a device having at its terminal portion, a "sharp tip," "tip," "probe tip," or "hard tip" as defined above.

Surface Chemical Analysis

One traditional method of surface chemical analysis of solids, which is widely known, is based on phenomenon of X-ray fluorescence excited by high energy electron bombardment. This method uses: (a) combination of scanning electron microscope (SEM) with X-ray spectrometer and comprises, (b) bombardment of solid sample in vacuum by sharply focused electron beam having high energy, and (c) recording energetic distribution of secondary X-ray quanta emitted from surface layer of the sample. The information provided by this method relates only to element composition of surface layer of the sample and tells nothing about its molecular composition. Moderate spatial resolution of this method is typically about few microns by the order of magnitude in all three dimensions because it is limited by physical peculiarities of high energy electron scattering occurring inside solid materials. Few more technical details have been published by R. Eckert, *Scanning*, v. 8(5), p. 232-238, 1986.

Another method of surface chemical analysis of solids, known as X-ray photoelectron spectroscopy (abbreviated typically as XPS). This aspect method requires an additional preliminary step: (a) providing vacuum technique, namely X-ray photoelectron spectrometer, capable of measuring kinetic energy of electrons. This method further comprises steps: (b) irradiation of the sample in vacuum by X-ray beam, and (c) measuring kinetic energy of secondary photoelectrons emitted from surface layer of solid sample. More details of this method can be found in the manuscript published by Nobel Prize winner K. Siegbahn et al: ESCA, Nova Acta Regiae Societatis Scientiarum Upsaliensis, UPPSALA, 1967 (Sweden).

The general information provided by this method also relates mainly to the elemental composition of the surface layer of a solid sample, said surface layer having thickness about 5-10 nm. At the same time, spatial resolution of this method in the plane of the sample's surface is defined by the cross-section of the excitatory X-beam, which isn't better than few microns even with most advanced XPS devices. However, some fine details of the information following from kinetic energy measurements may relate to surface molecular compounds as well because these details can be interpreted in terms of energy of chemical bonds participating in connection of surface atoms.

An additional traditional method of surface chemical analysis of solids is based on so-called Auger effect described in scientific literature (see, for example, Chuan C. Chang, *Surface Science*, Issue 1, p. 53-79, 1971). Both information abilities of Auger-method and its necessary steps (a, b, c) are similar to some extent to that of XPS method with the only significant difference that vacuum emission of secondary Auger-electrons initiated in step (b)

comprise irradiation of a surface layer of the sample in a vacuum by a high energy electron beam. Spatial resolution of Auger-methods are also comparable by an order of magnitude with that of XPS-method described above.

All three methods listed above have been known and used for many decades notwithstanding they have significant disadvantages. First of all, they all require at least high vacuum technique, and preferably ultrahigh vacuum technique, which is complicated and expensive. Second, in regard of chemical analysis of surface layers sensitivities of these methods are relatively low, and spatial resolution related to X-Y surface plane of samples cannot be made better than about 1000 nm by the order of magnitude whereas spatial resolution in Z-direction orthogonal to said surface plane cannot be made better than 5-10 nm. Third, these methods cannot be considered as non-destructive because they all are using high energy irradiation of samples (typically at least few KeV or more) so that any material suffers more or less under such a condition. The same combination of disadvantages is fully applicable to secondary ion mass spectrometry method (SIMS) of surface chemical analysis in which irradiation of solid sample in vacuum is performed by high energy (about 1 KeV) ion beam. Additional technical details of SIMS method can be found in papers published by A. Benninghoven, *Physica Status Solidi*, v. 34(2), p. K169-171, 1969 and S. Hofmann, *Phil. Trans. R. Soc. Lond.*, v. A362, p. 55-75, 2004.

Recently, a different new method of surface chemical analysis became known. This method is based on discovery of a new physical phenomenon, namely Tip Enhanced Raman Scattering abbreviated hereinafter as TERS. Discovery of TERS can be considered as a next scientific step in well known Raman spectroscopy, in which an analyzed object is to be illuminated by monochromatic primary light having fixed wavelength $\lambda_0$ and, correspondingly, fixed frequency $v_0$. In response to illumination, the object scatters the light. Secondary light scattered by the object is analyzed by optical spectrometry for recording spectral distribution of said scattered light. The point is that a certain fraction of the light scattered by the object may have different wavelengths $\lambda \neq \lambda_0$ corresponding to other frequencies $v \neq v_0$ so that differences $\Delta v \sim (v-v_0)$ reflect vibration frequencies of atoms and molecular groups contained in this object. Such differential frequencies $\Delta v$ are known to be very specific for each particular molecule, therefore traditional Raman spectroscopy belongs to wide family of different methods of chemical analysis. Taking into account that primary light falls typically into the visible wavelength range corresponding to low energy of light quanta, the traditional Raman spectroscopy is thought as non-destructive method of chemical analysis.

For more clarity block-diagram of a device performing a method of traditional Raman spectroscopy is depicted in FIG. 1 wherein most components participating in the method are numerated as follows: 1—a sample (called also "an object" above), 2—primary light beam having fixed wavelength $\lambda_0$ (shown as thick white arrow), 3—non-scattered or elastically scattered light component having the same wavelength $\lambda_0$ and the same frequency $v_0$ (also shown as thick white arrow), 4—a laser producing primary monochromatic light beam, 5—a lens collecting scattered light, 6—optical spectrometer combined with recording system 7 so that information flow (shown with dashed arrow 8) is transferred to a computer. The scattered light beams having other frequencies $v \neq v_0$ (shown with thick black arrows 9) is collected by the lens 5 and transferred to input slit 10 of optical spectrometer 6 for further spectral analysis.

Figure 2:
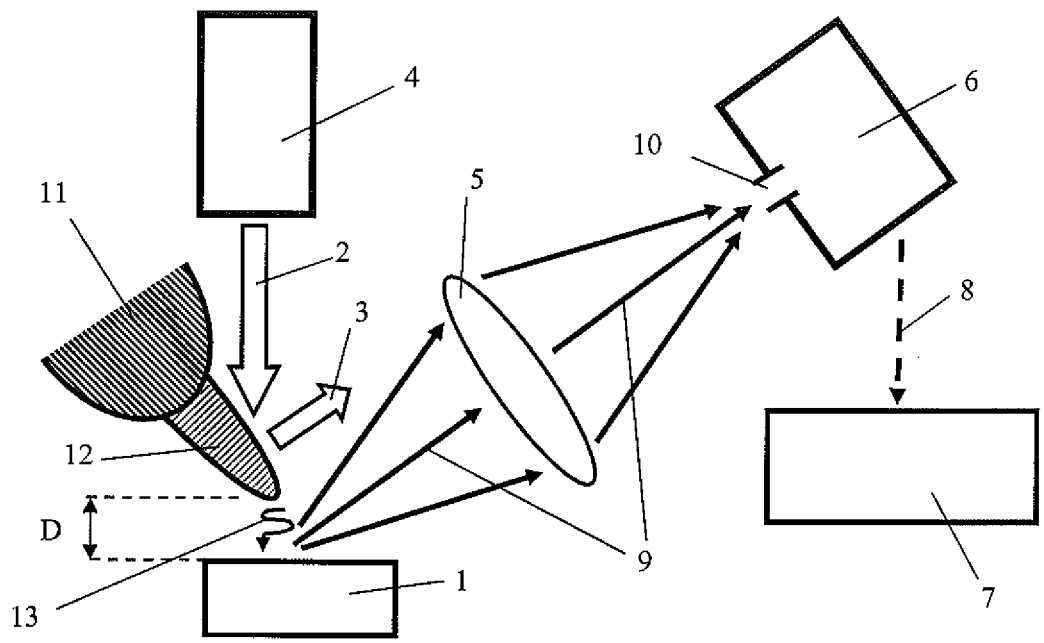
FIG. 2 depicts a general block-diagram of modified equipment for TERS spectroscopy.

However, prior Raman spectroscopy had relatively low sensitivity, which didn't allow using this method for high efficiency surface chemical analysis of solid samples. Discovery of phenomenon TERS changed this situation amazingly. There are two major features which make important difference between TERS and traditional Raman spectroscopy. The first major feature of TERS is that produced by the laser 4 primary light beam 2 is well focused onto sharp tip 12 of a needle 11 (FIG. 2), wherein said tip is made of a material containing appropriate concentration of free electrons. In other words, the tip appropriate for TERS must provide electric conductivity. In this case an intensity of focused primary light beam 2 can be made high enough to cause excitation of so-called plasmon oscillations of said free electrons so that frequencies of both a plasmon and primary light quanta are equal $v_0$. Another consequence of high intensity light illumination of sharp tip 12 and, correspondingly, the second major feature of TERS is that propagation of the plasmon along sharp tip is accompanied by appearance of extremely strong and well localized external electromagnetic field 13 having the same high frequency $v_0$ as primary light beam 2. This external field (shown in FIG. 2 as curly arrow 13) has rather limited volume concentrated in proximity of sharp edge of the tip 12. Typically this proximity is defined by low distance D between the tip 12 and the surface. At extremely low D the sharper end of the tip the better localization of the field 13 so that typical size of said high frequency electromagnetic field can be made as low as about 1 nm by the order of magnitude or, may be, even much less than 1 nm. Under such conditions any atomic group or any molecule located in the same proximity of the tip 12 becomes excited by localized strong field 13 and starts emitting secondary light quanta having specific frequencies $v$ related to this particular atomic group or molecule. Spectral analysis of these secondary light quanta performed by optical spectrometer 6 combined with recording system 7 gives the information regarding chemical nature of atoms and/or molecules involved into such emission of secondary quanta.

In comparison with traditional Raman spectrometry the first advantage of TERS approach is that, due to so high intensity of the field 13, both an efficiency of emitting secondary quanta having specific frequencies and, correspondingly, sensitivity of TERS are enhanced many million times. The second advantage of TERS is sharply increased spatial resolution of chemical analysis because such enhanced emission relates only to chemical species localized in extremely low volume related to proximity of sharp tip 12.

The three previous paragraphs have been provided to clarify physical principles of TERS phenomenon used as a basis for most advanced prior art methods of surface chemical analysis of solid samples. Practical approach described in scientific literature as prior art is depicted for clarity in FIG. 3 in the form of general block-diagram. At present moment two a little bit different versions of prior art methods are known and considered below. Now we start with discussion of first, more common group of methods based on first version used, for example, by Norihiko Hayozava et al (see *J. Raman Spectrosc.*, v. 43, p. 1177-1182, 2012). The prior art method reflecting this version comprises the following sequence of steps:

Step #1. Providing a device combining a scanning probe microscope 14 (SPM) with an optical spectrometer 6 and recording system 7, wherein a probe is made in the form of conducting needle 11 having sharp tip 12. Prior art devices are always supplied with a feedback system participating in automatic operation of said microscope while scanning so that at least one parameter of said microscope 14 is permanently kept constant. Programmable automatic operation of both the microscope 14 and recording system 7 is controlled by a computer 25. The devices known in prior art are also capable of:

(i) illuminating a sharp tip 12 of the needle 11 with focused laser beam 2;

(ii) collecting a light emitted from proximity of said sharp tip 12 (actually collecting both elastically scattered light component 3 and non-elastically scattered light 9 for spectrometric analysis provided by said optical spectrometer 6; and (iii) storing in memory both coordinates of the needle 11 and results of said analysis related to these coordinates.

Step #2. Initiating a regime of said scanning probe microscope 14 in which the tip 12 of the needle 11 touches firmly the surface of sample 1 to provide permanent mechanical contact. In order to stabilize such regime said feedback system automatically keeps chosen feedback parameter equal to a certain predetermined constant. In some embodiments of prior art, this feedback parameter is associated with a predetermined constant force of interaction between said tip and said surface so that resulting actual force corresponds to at least tight mechanical contact of the tip and the surface. In other embodiments of the prior art, said feedback parameter may relate to a predetermined constant tunnel current. In this case the tip 12 presses the sample 1 even tighter and the actual force of such enhanced electric contact is typically much higher than just force of tight mechanical contact.

Because the force of mechanical contact (typically about $10^{-8}$ N by an order of magnitude) is so high and effective area of typical tip 12 may be as low as about $10^{-14}$ cm$^2$ by an order of magnitude the continuous pressure applied by tip 12 to sample 1 may exceed $10^6$ N/cm$^2$ resulting in irreversible deformation of either the tip or the sample, or both. For example, any metal undergoes strong plastic deformation under continuous pressure exceeding $10^5$ N/cm$^2$.

Step #3. Moving the needle 11 continuously in the direction which is substantially parallel to surface X-Y plane of the sample 1 (see FIG. 4). In accordance with the only available regime established in the step #2 this moving occurs with a constant speed S simultaneously with permanent automatic keeping of predetermined feedback parameter. Correspondingly, either the tunnel current or the force of tight mechanical contact of the tip 12 with the surface of sample 1 remains constant while said moving. Because microscopic details of surface relief may be rather complicated, maintaining of either the constant force or constant tunnel current results in automatic constant displacement of the needle 11 relatively the sample in Z-direction which is substantially orthogonal to said surface. Dotted line 16 in FIG. 4 shows an example of expected ideal trajectory of the tip 12 of needle 11 in accordance with the only available regime provided by the step #2.

Figure 4:
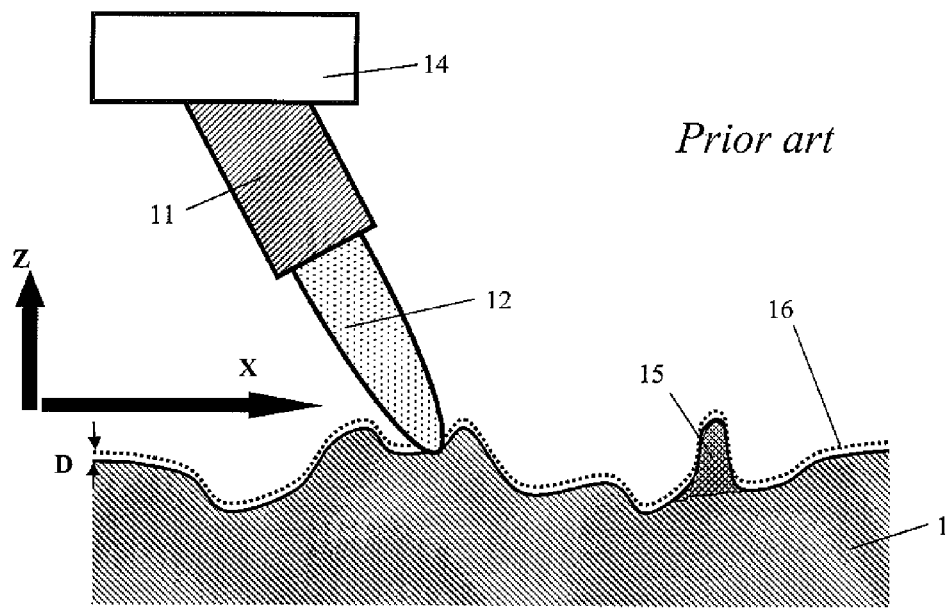
FIG. 4 depicts a trajectory of needle relocation used in typical regime of prior art method providing microscopic chemical analysis of samples having complicated surface relief.
Figure 5:
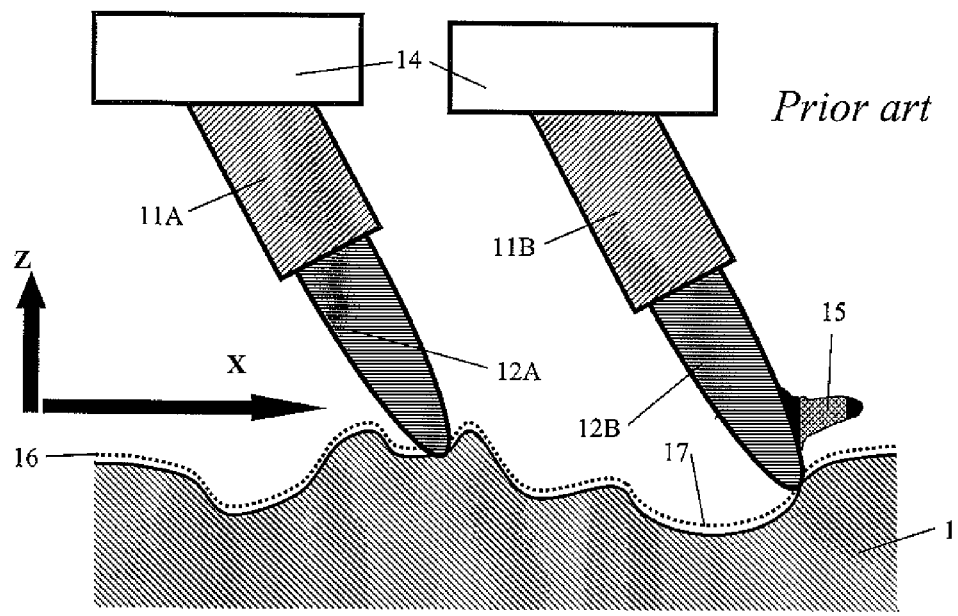
FIG. 5 depicts one of the disadvantages typical of prior art methods.

However, in reality the tip 12 moving continuously along the surface with simultaneous keeping both extremely low distance D and extremely high permanent pressure can work as a cutting instrument causing scratches 17 on the surface of sample 1 (compare ideal FIG. 4 and more realistic FIG. 5). Extremely low distance D corresponding to either constant mechanical or constant tunnel contact mentioned above is absolutely necessary price one has to pay in order to obtain sufficient sensitivity of chemical analysis because natural efficiency of TERS phenomenon depends strongly on said distance.

Step #4. Illuminating sharp tip 12 of needle 11 continuously with focused laser beam 2.

Step #5. Collecting the light emitted from proximity of said sharp tip 12 with simultaneous non-interrupted spectrometric analyzing of said light by said optical spectrometer 6. This step comprises accumulation of results of spectrometric analysis by recording system 7 for predetermined time interval. However, in prior art methods, there is no need to interrupt analyzing procedure because extremely low distance D between the tip 12 and the surface (see FIG. 3 and FIG. 4) remains constant with time.

Step #6. Storing results in memory of spectrometric information accumulated during step #5, together with mean coordinates of the needle 11 corresponding to relatively small local surface area of current analysis. Thus, results of spectrometric analysis reflect surface chemical composition in each small local surface area of sample 1 which is currently analyzed. The length of each small current local surface area of the analysis is defined by a product resulting from multiplication of said constant speed S of continuous moving (see step #3) by predetermined accumulation time (see step #5). An example depicted in FIG. 4 shows that certain small local surface area of the sample 1 may contain molecular cluster 15 which is chemically different from composition of other small surface areas. Correspondingly, memorized results of chemical analysis in this particular area are to be different from results related to other areas.

Step #7. Return to step #5 in order to provide surface chemical analysis in next small local surface area of the sample, said next area adjacent to local area already analyzed in step numbers 3-6.

Some positive features of prior art methods described above are as follows:

(i) In the ideal case, a microscopic resolution of chemical analysis in X-Y plane may be as high as about 1 nm by an order of magnitude.

(ii) Chemical information obtained relates only to extremely thin surface layer having thickness about 1 nm or less.

(iii) In some cases high sensitivity of microscopic chemical analysis may correspond to observation of small molecular clusters or even single molecules located on the surface and occupying negligibly small volume about 1 nm$^3$ by the order of magnitude.

It may be important to stress for further discussion and deep understanding of the nature of present invention that typical for prior art tight contact is kept continuously for relatively long time required to complete scanning of chosen area of the sample. For example, in order to create microscopic TERS image containing rather low number 100×100 points the prior art method requires scanning for at least 2 minutes even if accumulation of chemical information in step #5 takes only as low as about 0.01 s per point. That is why continuous tight contact causing extremely high surface pressure in steps #2 and #3 of prior art cannot be made shorter in time than about 2 minutes, and practically it takes much longer time when more detailed microscopic imaging is required.

However, this group of more common methods of the prior art cannot be considered as non-destructive methods of surface chemical analysis because this group contains some intrinsic negative. These important disadvantages are listed below:

(a) Maintaining a tight mechanical contact between the sample 1 and the tip 12 made of hard material results in too strong a force applied to sample's surface permanently while scanning. This high force may cause irreversible damage to the sample, especially in cases when either all parts of the sample or some of its parts are softer than the tip 12. Correspondingly, information regarding chemical state of the sample's surface becomes irreproducible. Comparison of FIG. 4 and FIG. 5 demonstrates an example of such partial damage caused by cutting effect of rather strong permanent pressure applied by sharp tip 12 while its continuous moving along the surface from position 12A to position 12B.

(b) The damages mentioned in point (a) immediately above are a result of surface scratching caused by moving hard tip 12 along the surface relief simultaneously with application of strong compressive pressure. This scratching leads to non-controllable relocation of microscopic portions of surface material so that at least some chemical particles located initially on the surface may be relocated to other surface points and further adhered to the tip 12 as, for example, molecular cluster 15 in FIG. 5. In fact, movement of the tip 12 together with adherent cluster 15 is equivalent to the use of dirty needle 11 contaminated unpredictably with unknown chemical compounds. However, this contamination occurs in proximity of the tip 12 where chemical information is produced in the form of non-elastically scattered light. If such non-controllable contamination occurs in the step numbers 4, 5, and 6 of prior art methods, the result will be not controllable and incorrect chemical information in regard of such points of sample's surface where this cluster 15 has never been before.

Figure 6:
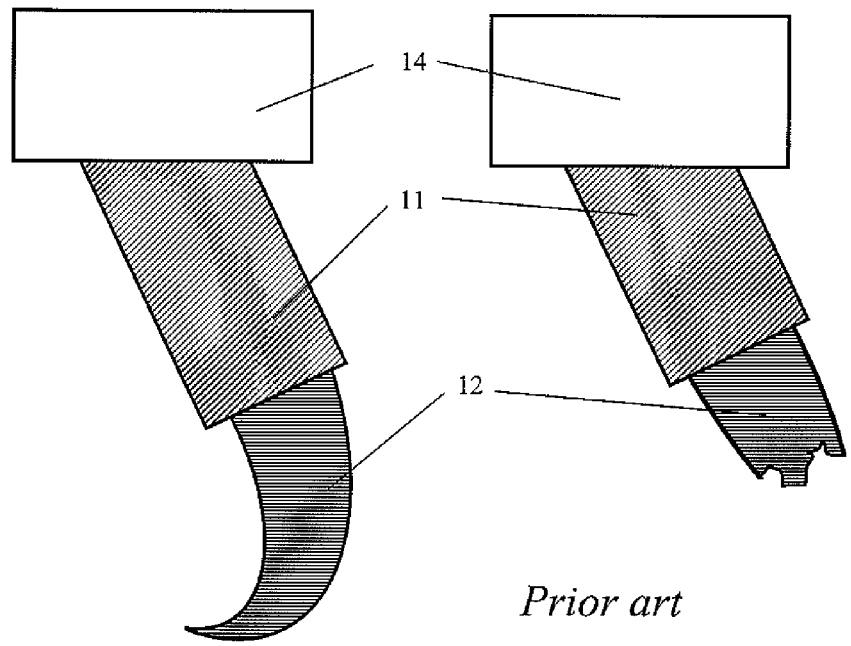
FIG. 6 depicts another disadvantage typical of prior art methods.

(c) Strong compressive force applied permanently to the needle 11 in all step numbers 2-7 of prior art methods may also result in irreversible and practically non-controllable damage to the tip 12 while scanning if whole sample or some its parts are harder than the tip 12. In this case the tip 12 can be either deformed as shown on left side of FIG. 6 or broken completely (see right side of FIG. 6). Regardless of what kind of damage occurs, such damage leads to serious violation of optimal conditions of surface chemical analysis and, correspondingly, results in either lost spatial resolution or decreased sensitivity, or both. In any case this situation leads to incorrect and non-reproducible results.

Some disadvantages mentioned above related to potential damages and poor reproducibility may be either reduced or eliminated in second version of prior art methods. This less common version (see for example a paper by E. Bailo, V. Deckert, *Angew. Chem. Int. Ed.*, v. 47, p. 1658-1661, 2008) differs from the first one in the only respect that a step #2 doesn't initiate permanent mechanical contact between the tip 12 of the needle 11 and the sample 1. Instead, in the second version the step #2 initiates permanent work of said scanning probe microscope 14 in so-called tapping regime in which the tip 12 of the needle 11 oscillates in Z-direction while scanning. This oscillation occurs with as high frequency as about $10^5$ Hz by the order of magnitude, and high amplitude which is typically in between 5 nm and 50 nm. In this case said feedback system automatically keeps chosen predetermined feedback parameter related only to either an amplitude or a frequency of said oscillations. It remains unknown in such regime whether there are even short time moments when the tip 12 is capable of reaching said extremely low distance D which is necessary for proper recording TERS phenomenon. It has to be noted that typically most appropriate for TERS extremely low distance D doesn't exceed couple nanometers, and desirably is even less than 1 nm corresponding to at least tight mechanical contact of the tip and the surface of sample 1. However it should be appreciated by anyone of ordinary skill in the art that in said regime of high frequency oscillation having high amplitude the tip 12 can get momentary position closest to sample's surface only for extremely low fraction of a period of said oscillation whereas the tip 12 is spending main part of said period far away from the sample. That is why the second version of prior art method always results in either negligibly low sensitivity of TERS analysis provided in reasonable time or unacceptably long time of chemical imaging when modest TERS sensitivity is required. As a result main disadvantage of second version of prior art methods is their rather poor reproducibility.

Another disadvantage of practically all versions of prior art methods, including both common version described above, is that they doesn't provide as high chemical sensitivity as can be expected in principle on the basis of TERS phenomenon. The point is that existing methods don't take into account that the nature of samples may be different and the tip 12 can be made of multiple materials having different physical properties. However, prior to the present invention, there are no theoretical or experimental bases to support the notion that only a tight direct mechanical contact between the tip 12 and sample's surface provides the best efficiency of TERS analysis, independently of potential variations of material of the tip and physical nature of the sample. The systems, devices, and methods disclosed herein address these problems and for the first time, permit accurate, reproducible, sensitive, and spatially accurate analyses of surfaces using TERS.

Description of Embodiments

We have identified a new problem in the art, namely, how to provide systems, devices, and methods that can be used to determine chemical identities of substances on the surface of a solid object. Additionally, we have provided new systems, devices and methods to achieve this important result. In certain aspects, the invention uses a computer processor comprising computer memory, programmed to accept, store, and analyze information obtained using optical and mechanical devices as described herein. Other descriptions of embodiments can be found in U.S. Utility patent application Ser. No. 14/717,336 filed 20 May 2015, the contents of which are herein fully incorporated by reference.

Technical Features of Devices for Step (a) of the Invention

Figure 3:
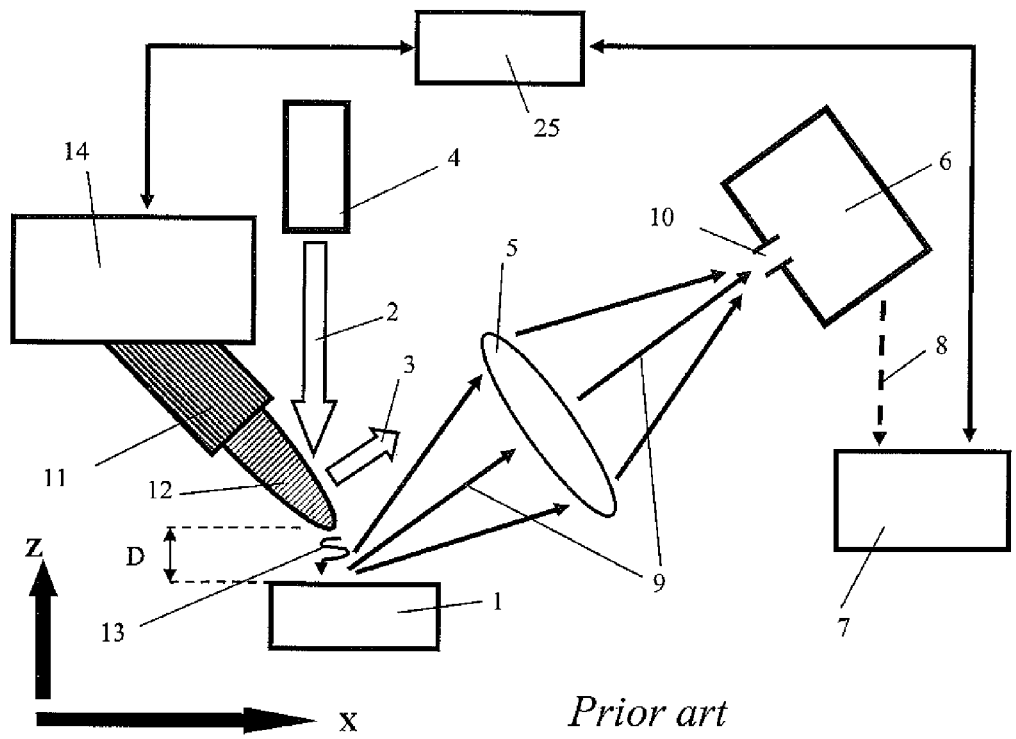
FIG. 3 depicts a general block-diagram of equipment used for the method of the invention.

Non-destructive methods of surface chemical analysis of the present invention are based on use of a device comprising a scanning probe microscope (SPM) 14 operably linked with an optical spectrometer 6 which is connected with recording system 7 accordingly to general block-diagram depicted in FIG. 3. Additional technical details of the same equipment are shown also in FIG. 7 and FIG. 12. SPM 14 is programmatically operated mechanism which is capable of moving either a probe 18 or a sample 1 for changing position of the probe 18 relatively the sample 1 in any of three dimensions. Due to technical designs of SPM 14 may be different, in some embodiments of the invention the sample 1 can be capable of moving in any of three dimensions relatively immovable probe 18, and in other embodiments of the invention the probe 18 can be capable of moving in any of three dimensions relatively immovable sample 1. However, any person of ordinary skill in the art should appreciate that the method of present invention considers only relative movement of said two elements and is equally applicable to both these cases of technically different SPM 14.

Figure 7:
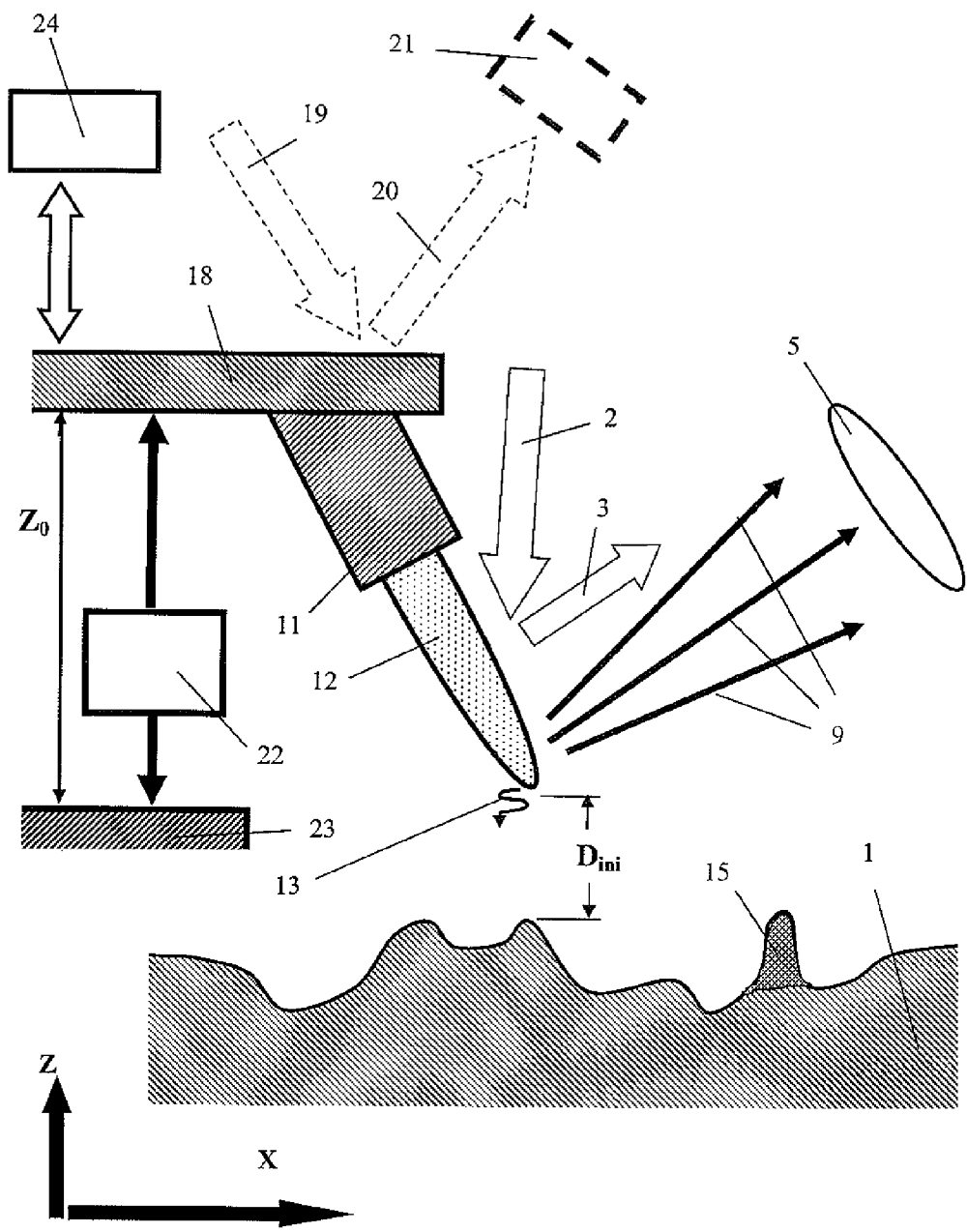
FIG. 7 depicts additional technical details of a device used for the method of the invention.
Figure 11:
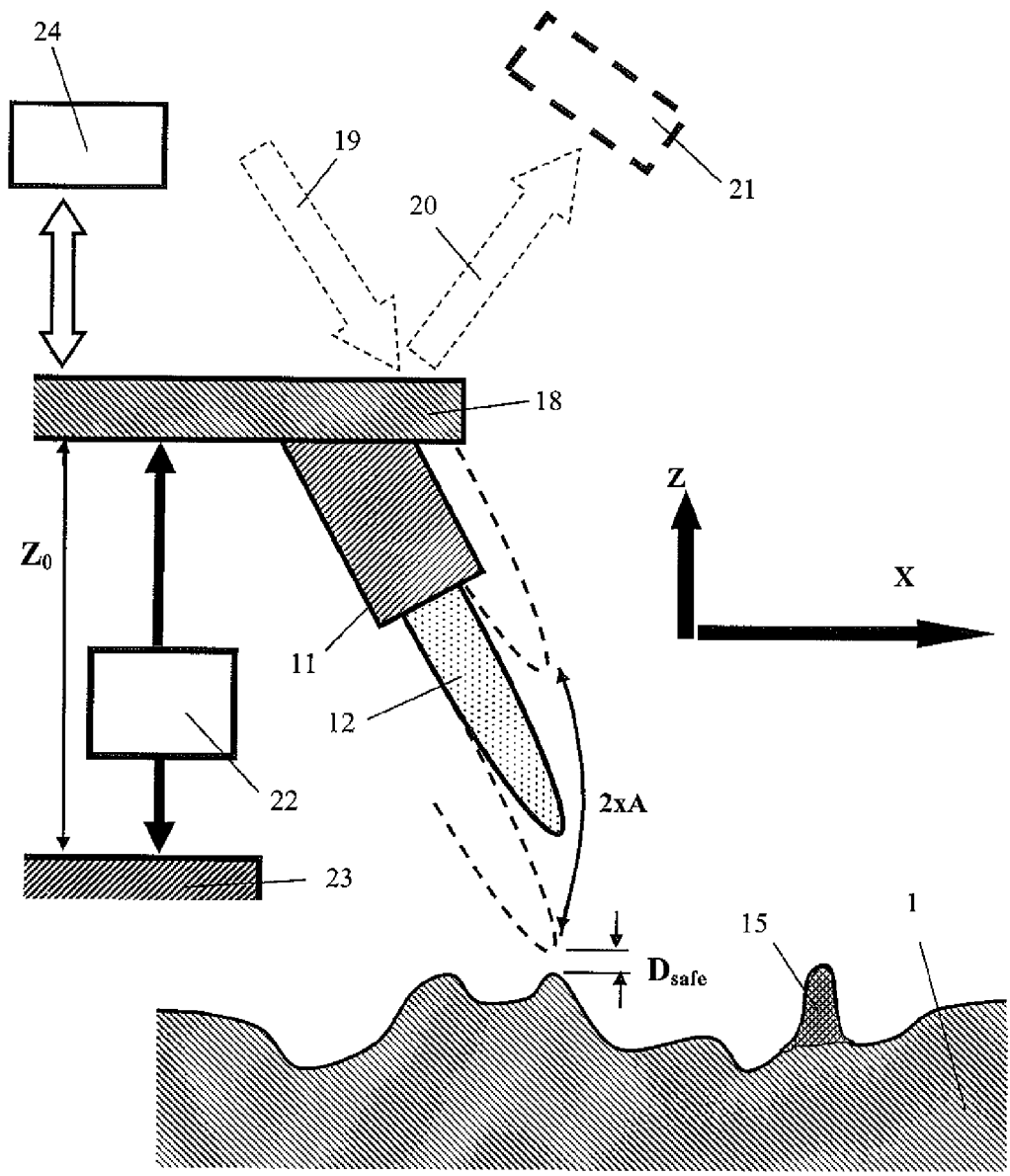
FIG. 11 depicts oscillation of the probe in the first safe regime of intermittent contact.
Figure 12:
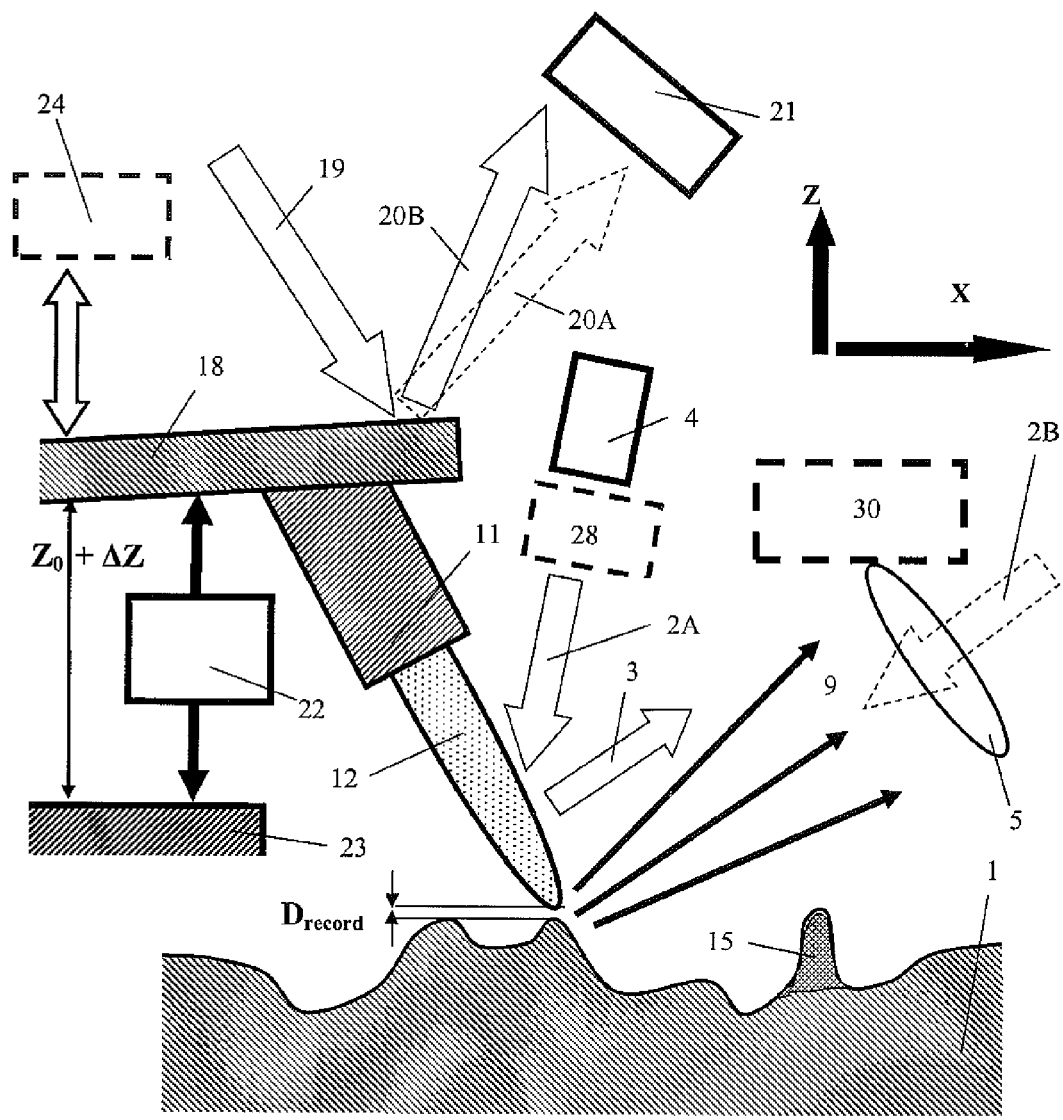
FIG. 12 depicts position of the probe relatively the sample in the second regime of TERS chemical analysis of chosen surface point.

Different probes 18 can be used but in any case the probe 18 of present invention must comprise the needle 11 supplied with sharp tip 12 having appropriate concentration of free electrons. The device used must also be supplied with a laser 4 producing primary light beam 2 which is focused onto sharp tip 12 in order to excite plasmons resulting in appearance of strong high frequency electromagnetic field 13 near the end of this tip. It has to be noted here that FIG. 7, FIG. 11 and FIG. 12 are simplified intentionally in order to provide most clear schematic explanation of main principles of the invention. That is why neither simplified FIG. 7 nor simplified FIG. 11 and FIG. 12 show either optical or opto-mechanical elements which are absolutely necessary to provide said fine focusing of primary light beam 2 on sharp tip 12. However, it should be appreciated by any of ordinary skill in the art that the presence of such opto-mechanical elements is silently assumed within the scope of present invention because it logically follows from previously described main physical idea of TERS analysis. It obviously follows also that the device of the invention is desirably capable of automatic relocating of focus point of the primary light beam 2 simultaneously with spatial relocation of sharp tip 12 while scanning of the surface of sample 1 and/or while preparation for said scanning. Such capability may be important even in the case of SPM equipped with immovable probe 18 because it allows automatic compensating of thermal expansion of said probe while its illumination with high intensity primary light beam 2. Automatic relocating of focus point of the primary light beam 2 can be achieved if the device of the invention comprises a mechanism capable of automatically relocating focus point of the beam 2 accordingly to controlling signals of the computer 25. For example only, such electronically controlled mechanism can comprise a piezoelectric scanner connected mechanically with at least one optic element such as either lenses or mirrors which define spatial position of focus point of primary laser beam 2. For example only, FIG. 12 demonstrates an optional embodiment of the device of the invention in which the lens 5 is controlled by piezoelectric scanning mechanism 30 and primary laser beam 2B (shown with dashed arrow) is directed to pass through the same lens 5. Detailed explanation of this design is provided a little bit later. It should be appreciated by anyone of ordinary skill in the art that general scope of the invention doesn't depend on whether such scanner or another mechanism is present or not but its presence is quite desirable because it helps to improve stability of illumination of the tip 12 and increases sensitivity and efficiency of TERS analysis.

The scanner causing said mechanical movements of optical element(s) focusing the beam 2 is fully controlled by electric signals sometimes up to hundred volts produced in special box called electronic controller. This electronic controller is a slave which fully obeys relatively week commands produced by a computer as a master. However, the controller may have its own software which cooperates with computer software. In any case the whole operating system of SPM consisting of combination of both the controller and the computer can work properly only if this operation occurs in real time. Of course, actual values of real time operations are always stored in computer's memory accordingly to its software and/or settings determined by an operator before beginning of scanning. It doesn't matter where real time signals are formed—whether in the computer or in the electronic controller.

Mechanical precision of piezoelectric scanner can be extremely high—so, theoretically there is no problem to make as low shift of the probe in any of three dimensions as fraction of Angstrom. But at the same time a behavior of typical piezoceramic undergoes additional internal relaxation processes which occur in time and are not well controlled by external electric signals. By the term "relatively rough," we mean this theoretic high precision combined with said practical complications which are not fully predictable.

The secondary light scattered from proximity of the tip 12 includes both not useful elastically scattered light component 3 and non-elastically scattered light beams 9 which may contain useful chemical information. Optical element(s) 5 such as lens or, for example, mirror are used to collect all light beams emitted from proximity of sharp tip 12 for spectrometric analysis provided by optical spectrometer 6. It should be clear from viewpoint of a sensitivity of the device that the best results can be obtained if proximity of sharp tip 12 is kept in focus point of optical element 5. Results of said spectrometric analysis are recorded by system 7 and reflect chemical composition of a substance located within extremely low volume in proximity of the tip 12. It should be appreciated by anyone of ordinary skill in the art that in the same frame of general scope of the invention it may be quite desirable that at least one collecting optical element 5 is also controlled by piezoelectric scanning mechanism similar to one described in previous paragraph. As mentioned before such optional scanning mechanism is silently assumed within the scope of present invention by the main idea of TERS analysis even if it is not shown on simplified FIG. 7 and FIG. 11. However in FIG. 12 this scanning mechanism having number 30 is depicted schematically as dashed rectangular. The reason for that is that spatial position of extremely small local volume emitting non-elastically scattered light beams 9 may relocate simultaneously with spatial relocation of sharp tip 12 while both scanning of sample 1 and/or thermal expansion of the probe 18. That is why the presence of piezoelectric scanning mechanism 30 operably linked with computer 25 and controlling at least one optic element 5 while scanning may improve efficiency of collecting non-elastically scattered light beams 9 and increase sensitivity of TERS analysis.

Devices of the invention can be designed so that primary laser beam 2 and emitted light beam 9 have quite different spatial orientation as shown, for example, by solid arrow 2A and arrows 9 in FIG. 12. However in framework of the same scope of present invention a specific design of some other devices can permit coaxial orientation of both the beam 9 emitted from proximity of sharp tip 12 and at least final part of primary laser beam 2. The point is that the beam 2 needs to be focused exactly to the same point of sharp tip 12 which emits the beam 9 containing chemical information. That means that optic element 5 can be used for both aims, namely for proper focusing primary laser beam 2 and collecting the emitted light 9 for further transportation of emitted light to optical spectrometer 6 for chemical analysis. Definitely in this optional case both these beams 2 and 9 must have opposite direction of propagation through the element 5 made in the form of transparent lens as shown, for example, by dashed arrow 2B and arrows 9 in FIG. 12. An obvious advantage of this optional design is that required fine focusing of both beams 2B and 9 can be provided by the same optic element 5, and the only optional piezoelectric scanner 30 is required in order to control position of focus points of both said beams 2 and 9 while scanning of the sample.

A programmable, controlled recording system 7 can also store in memory all three coordinates related to current position of probe 18 relatively the sample 1 at any moment of the analysis. It has to be stressed one more time that, taking into account that mentioned before design of SPM 14 may be different, in present invention words "coordinates of current position of probe 18" are always understood as coordinates of probe 18 relatively the surface of the sample 1 independently on whether the mechanism of SPM 14 causes actual relocation of the sample 1 relatively immovable probe 18 or actual relocation of the probe 18 relatively immovable sample 1. Hereinafter coordinates X and Y are considered as coordinates of X-Y plane which is substantially parallel to the surface of sample 1. At the same time the coordinate Z is substantially orthogonal to X-Y plane and is considered hereinafter as a variable associated with a distance D between the tip 12 and the surface of sample 1. At any time moment the information regarding current X-, Y-, and Z-coordinates of the probe 18 is kept in controlling computer 25 (see FIG. 3) which defines programmatically all actions of both the microscope 14 and recording system 7.

It may be desirable in advanced and precise embodiments, that a scanning mechanism of SPM 14 providing X, Y, and Z relocations of the probe 18 relatively the sample 1 is supplied with special either distance or coordinate sensor system 22 which is capable of measuring variable Z-position of the probe 18 relatively certain immovable element, for example such as stable base 23 (see FIG. 7) or immovable sample 1, and directing this information to controlling computer 25 shown in FIG. 3. For example, coordinate sensor system 22 may be a capacitance sensor having sensitivity better than 0.01 nm. It may be desirable also that the microscope 14 is supplied with similar distance sensors related to X and Y coordinates.

Presence of an advanced type of coordinate sensor system 22 in design of SPM 14 is especially desirable wherein the probe 18 is represented by a piezoelectric resonator. For example, this may be a quartz resonator having U-form. Such implementation of quartz U-resonator for the use in SPM applications is often called as "tuning fork." In this case the needle 11 is to be connected with one leg of two of said U-resonator (FIG. 7 shows only one leg of the probe 18 for simplicity). It can be noted that SPM 14 charged with either U-form probe 18 containing quartz resonator or other type of piezoelectric resonator can be also supplied with electronic system 24 capable of both exciting oscillation of the needle 11 and accepting piezoelectric signals produced by deformed probe 18. This 2-way electronic communication between the probe 18 and the system 24 is shown in FIG. 7 as double-directed thick white arrow. Piezoelectric response signals created by either "tuning fork" or other type of piezoelectric resonator and received by electronic system 24 is usually used as feedback signal for SPM operation while scanning the surface of the sample 1.

In other embodiments, probe 18 can be made in the form of traditional cantilever having light reflecting area on its free end. In this case electronic system 24 supplied with piezoelectric element is used only to excite oscillation of said free end whereas a feedback signal is created by another system 21 supplied with multi-segment optical detector. In order to do so the light reflecting free end of the probe 18 is illuminated by another focused laser beam 19 whereas deflection or other deformation of said free end is optically detected as deviation of reflected beam 20. Note that elements 19, 20, and 21 are used for SPM operation only and don't participate in TERS measurements directly. In FIG. 7 elements 19, 20, and 21 are shown with dashed lines in order to stress that optical detection of deformation of the probe 18 is just an option depending on what kind of the probe is used in each particular case. However the use of either distance or coordinate sensor system 22 can be appreciated because it increases precision of SPM operation and make results more reproducible.

Now we have to discuss an additional novel technical feature of present invention which makes a principal difference between the invention and prior art methods. The point is that in prior art methods scanning regime of any SPM, and correspondingly, the regime of obtaining chemical information by a device depicted in FIG. 3, is defined by current combination of setting parameters kept constant by controlling computer 25 while scanning of the sample 1. In prior art methods this combination of setting parameters is established by the user before beginning of scanning and doesn't change during scanning process. That means that at least one important setting parameter, for example certain predetermined value of feedback signal, is permanently kept constant during scan in prior art methods. The result is that in both versions of prior art methods only one desirable regime of microscope 14 operations is used for both relocation of the needle 11 along the surface and accumulation of chemical information by recording system 7.

In contrast to the prior art methods, the systems, devices, and methods of the present invention comprise a scanning probe microscope 14 that can be capable of periodic programmable switching of at least one setting parameter while scanning, so that it results in periodic switching between at least two different regimes of microscope operation. The first regime of said two regimes of microscope 14 operations is aimed to provide safe preliminary observation of certain chosen point of sample's surface and to get preliminary setting information necessary for safe operation in second regime, whereas the second regime is characterized by changing at least one setting parameter of microscope 14 so that safe obtaining of chemical information from the same chosen point becomes possible. Correspondingly the recording system 7 of the device of the invention must be capable of correlating accumulation of chemical data in accordance with switching said two regimes of microscope 14. This correlation may be provided in different forms, including but not limited to interruption of data accumulation while the first regime providing preliminary observation of certain chosen point of sample's surface. It should be also appreciated that saying word "safe" in regard of both said regimes authors of present invention mean such two regimes of microscope 14 operations that neither the sample 1 nor the probe 18 (including its sharp tip 12) can be damaged in each of two said regimes.

It has to be noted that the device of the invention can be supplied with rather desirable optional system 28 (shown in FIG. 12 as dashed rectangular) which is capable of periodic interruption of primary light beam 2 (either the beam 2A in certain embodiments or the beam 2B in another embodiments), said beam interruptions synchronized with said switching regimes of SPM 14 operations mentioned before. The presence of such optional system 28 doesn't change the scope of the invention but can create certain specific advantages discussed later.

Thus, step (a) of present invention provides systems, devices, and methods in which all necessary technical features mentioned in this section are combined together.

Advantages of the Present Invention Over Prior Art

The disadvantages of prior art methods, such as irreproducibility of results and damage to either the probe or the sample, or both, originate from natural combination of three following factors:

1. Highly effective microscopic surface chemical analysis, such as for example TERS analysis or alike, requires typically extremely low distance D between the tip 12 of the needle 11 and the surface of the sample 1. In most cases D must be much less than 1 nm, for example it requires D about 0.1 nm or less. Hereinafter all quantitative estimates of physical and technical parameters are given in present specification in assumption that typical sharp tip 12 has very low curvature radius expressed in nanometer units.

2. Because results of each individual point-like surface chemical analysis relate to extremely low area (about or less than 1 $nm^2$) the analysis of full surface includes plurality of points and whole analytical procedure takes substantial time (typically many minutes) even with as low full area of surface analysis as about 100×100 $nm^2$.

3. In framework of operations typical for prior art methods any attempt to keep such low D continuously results in so strong force F of interaction between the probe and the surface (typically about $10^{-8}$ N) and so high local pressure (typically above $10^6$ $N/cm^2$) which can cause irreparable damage to either the sample or the probe, or both. In the case of TERS measurements combined with simultaneous high frequency oscillation of the probe the interaction force F is not so strong but the sensitivity becomes so low that chemical identification becomes irreproducible in most cases.

Therefore, we searched for ways to avoid the disadvantages of the prior art, and developed systems, devices, and methods which can result in real-time, continuously adjust force F of interaction of the probe with the surface even if the distance D between them remains as low as required accordingly to the point 1 above.

We have carried out a series of experiments and made a first discovery and its application that at most typical ambient conditions, (including but not limited to the temperature, atmospheric pressure, etc.), the mentioned above force F strongly depends on both the distance D and contact time $\tau_{cont}$. We found that even in the case of as sharp tip 12 as possible and extremely low D corresponding to mechanical contact an initial F (at $\tau_{cont}=0$) can be significantly reduced and made relatively low in between $10^{-9}$ N and $10^{-10}$ N by the order of magnitude. At increased contact time $\tau_{cont}>0$ and constant D mentioned above this force increases gradually in time and becomes stationary value up to about $10^{-8}$ N by an order of magnitude in a relatively short saturation time $\tau_{sat}$, which is typically in between 1 and 10 seconds. The dependence of saturation time on external conditions and materials brought in contact is not fully understood, but having discovered the phenomenon and how to adjust conditions in real time provides a distinct improvement in TERS analysis of chemical components, with reduced damage to the sample or equipment, and with increased sensitivity, and increased spatial resolution.

These experiments revealed a correct direction for development of non-destructive methods of the present invention for microscopic surface chemical analysis. Experiments resulted in another important discovery that either negligibly low damage or no damage at all are produced in most cases to both sharp tip 12 and typical solid samples like metals or silicon if duration of mechanical contact $\tau_{cont}$ executed in each particular point of sample's surface is limited accordingly to condition $\tau_{cont} \ll \tau_{sat}$. Therefore a physical principle of non-destructive method of present invention can be expressed as follows.

The time of mechanical contact $\tau_{cont}$ of the tip 12 and the sample 1 must be shorter than saturation time $\tau_{sat}$. The softer material of the sample the shorter duration $\tau_{cont}$ of mechanical contact between sharp tip 12 and sample's surface. For many practical applications a condition $\tau_{cont} \leq 0.2$ sec may be used in multiple cases of relatively hard samples, and more restrictive condition $\tau_{cont} \leq 0.05$ sec may be desirable from time to time to explore softer samples. However, exact numeric limits of $\tau_{cont}$ are provided above for example only, and different limitations of $\tau_{cont}$ can be used as well, depending on each particular combination of both the sample and the tip 12. For example, even contact time as short as $\tau_{cont}$ in between 0.001 sec and 0.01 sec may be used in some specific cases.

It has to be noted that certain specific devices of present invention allow further decreasing said contact time approximately one order of magnitude in comparison with prior art devices so that desirable $\tau_{cont}$ may be in between 0.01 sec and 0.0001 sec. Obvious advantage of these devices discussed later in more details is that they can combine increased sensitivity of TERS analysis with significantly increased speed of scanning and, correspondingly, shortened time of analysis of full chosen area of the sample 1.

Figure 8:
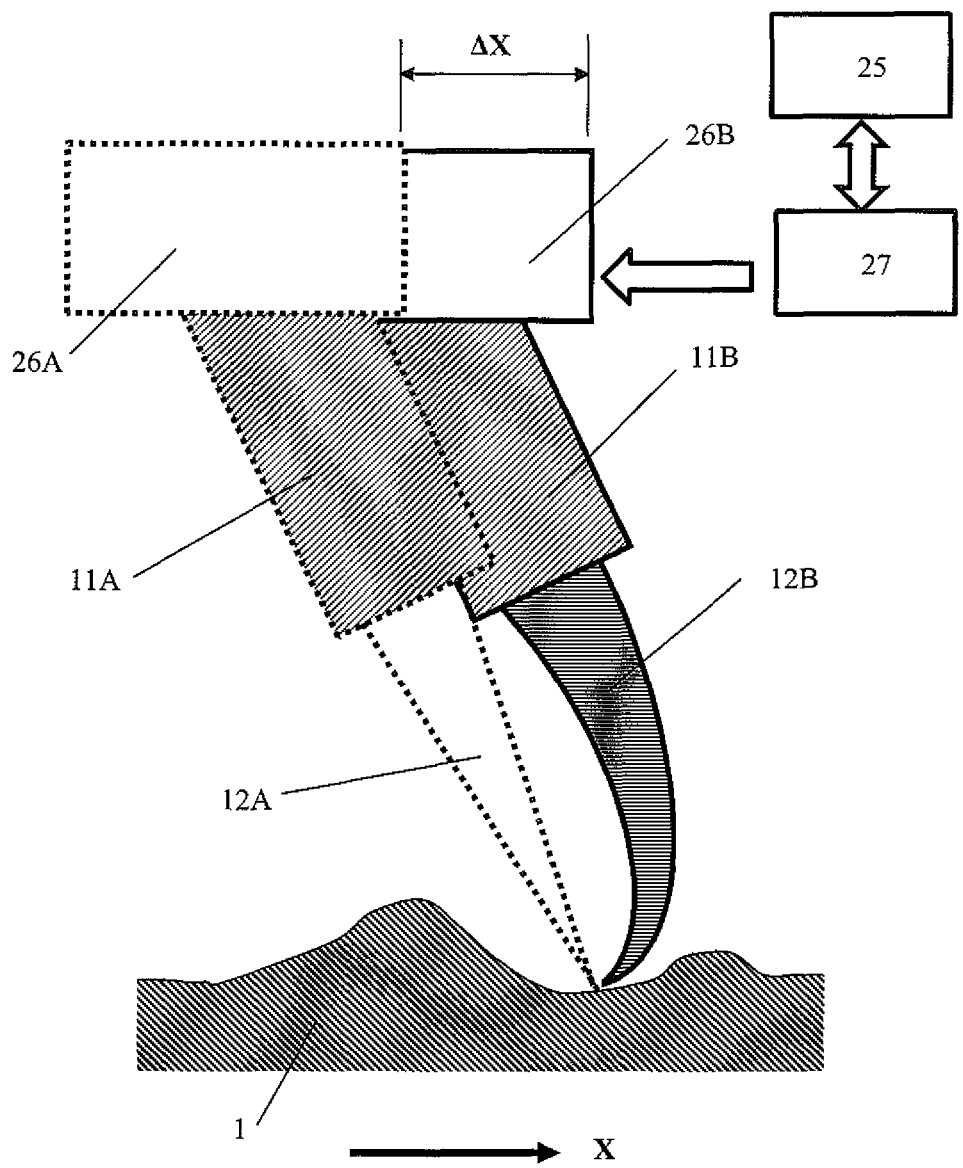
FIG. 8 depicts short-term elastic deformation of the probe while continuous scanning if the probe contacts the surface for limited contact time.

We made another discovery and its application, that non-destructive TERS surface chemical analysis can be done successfully if during short $\tau_{cont}$ the needle 11 moves relatively the surface of the sample 1 with as low relative velocity as possible. In an ideal case causing practically no damage, it may be desirable that during $\tau_{cont}$ sharp tip 12 of the needle 11 doesn't move relatively the surface of the sample 1 at all. FIG. 8 demonstrates such a possibility, which uses elastic properties of sharp tip 12. FIG. 8 shows positions of elements of SPM, namely a scanner 26, the needle 11, and its tip 12, at two different time states A and B, where the time state A corresponds to the very beginning of the contact time $\tau_{cont}$ and the time state B corresponds to the end of short contact time $\tau_{cont}$. For better visualization in time state A all elements are shown with dotted lines, and the same elements in time state B are shown with solid lines.

One can appreciate that at the beginning of the contact, sharp tip 12A is not deformed. In this initial moment A, mechanical contact is already established and the pressure applied by the tip to the sample 1 is accompanied by immediate appearance of a tangential friction force which holds the lower part of the tip 12 in the same contact point all the time. If scanner 26 moves in X-direction, it shifts the upper part of the needle 11 so that at final contact moment B, this shift is equal $\Delta X=S\tau_{cont}$ wherein S is predetermined speed of scanning. The shift of upper part of the needle (position 11B) and fixed contact position of its lower part (namely contact point of the tip 12B) results in certain deformation of the tip 12B as shown in FIG. 8. This deformation is proportional to $\Delta X=S\tau_{cont}$ and is non-destructive elastic deformation if $\Delta X$ is low enough. In order to keep such deformation low in safe brackets of non-destructive elastic deformation and prevent damage of either sample or the probe, one can use either low speed S or low $\tau_{cont}$, or low both parameters. It has to be stressed that the value of the shift $\Delta X$ expressed above depends on the speed S established during said contact time only because in some embodiments of the invention discussed later the speed of scanning during non-contact time may be different from said S. In other embodiments the speed S may be kept constant in both contact and non-contact time.

As a quantitative example only, one can choose a moderate scanning speed S=1 micron/sec and low $\tau_{cont}=0.003$ sec. In this case the deformation of whole needle 11 can remain a non-destructive elastic deformation because it doesn't exceed a low value $\Delta X=3$ nm which is few orders of magnitude less than full length of the needle (typically about 10 microns). On the other hand, this example explains why typical for prior art method long $\tau_{cont}>1$ sec leads to much higher deformation ΔX>1 micron. Such high deformation exceeds brackets of elastic deformation, and can result in either a broken tip (see FIG. 6) or scratched sample (see FIG. 5). As a result of the second discovery, we came to a conclusion that non-destructive TERS surface chemical analysis can be made based on two modifications.

Figure 9:
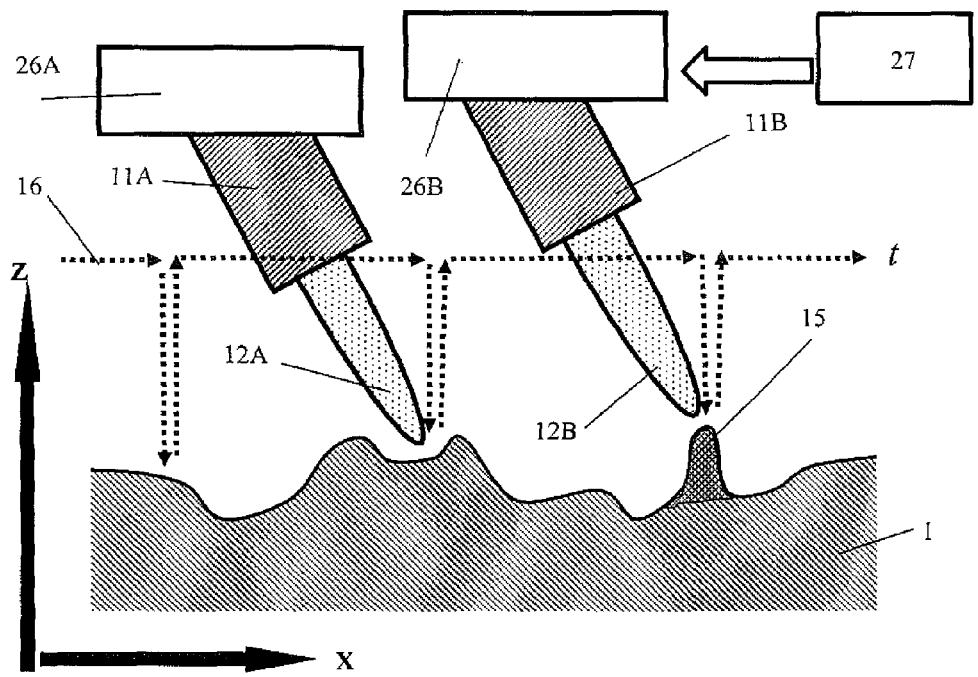
FIG. 9 depicts trajectory of non-destructive movement of the probe used in one of few modifications of the method of the invention.

One modification of the method allows keeping relatively high or moderate constant scanning speed S in the case of rather short contact time $\tau_{cont}$ which is desirably shorter than 0.03 sec by an order of magnitude. That means that transition of the tip 12 between adjacent points of analysis in time can be done accordingly to a diagram shown in FIG. 9, wherein the trajectory of movement of tip 12 from point-to-point is shown with a dotted line. At each point of the analysis, short contact time $\tau_{cont}$ corresponds to decreased distance between the tip and sample's surface, whereas transition from one point to the next one occurs at safely higher distance to avoid potential damage. FIG. 9 shows also that in this modification the time of surface analysis may be shorter than point-to-point transition time.

Figure 10:
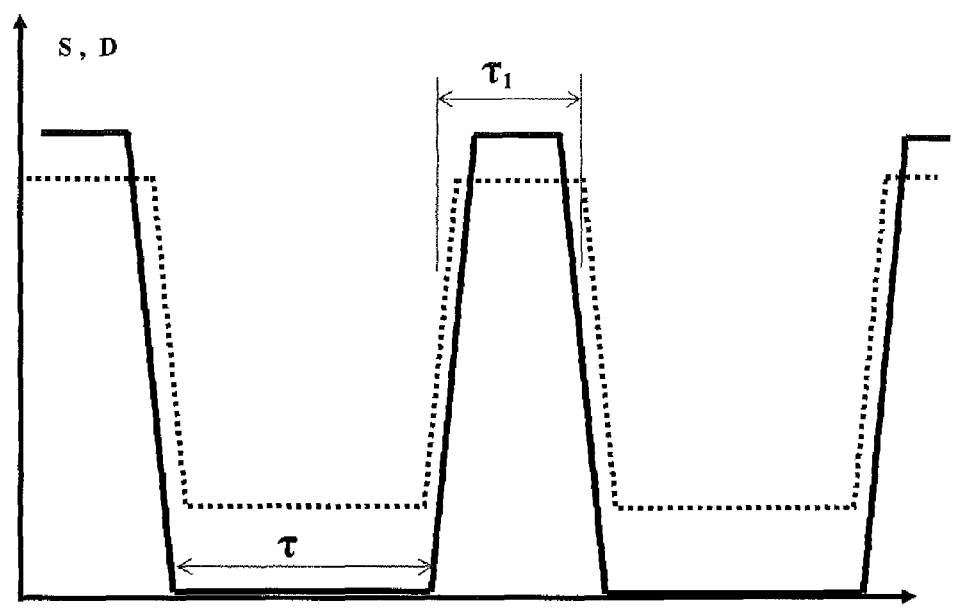
FIG. 10 depicts time-diagrams of scanning speed (solid line) and the distance between the probe and the sample (dotted line) in another modification of the method of the invention.

Another modification of the method can be desirable if non-destructive TERS surface chemical analysis of particular sample requires increased $\tau_{cont}$>>0.03 sec. In this case, it can be desirable that during $\tau_{cont}$ in each particular point of surface analysis, the scanning speed S is greatly reduced, and even more desirable S is made equal zero during $\tau_{cont}$. However, in order for complete analysis of a full sample area in reasonable time, one can interrupt contacts periodically and provide high speed transition of the probe from one surface point to next one during non-contact transition time $\tau_1$. In this modification the scanning speed S can be changed periodically as shown in time-diagram of FIG. 10, wherein dependence S(t) is represented by a solid line, and the dotted line shows the dependence D(t) for distance between the tip 12 and the surface of the sample. For simplification of FIG. 10 said above contact time interval is shown as $\tau_2$.

The novel and non-obvious discoveries are self-consistent in such respect that in order to provide non-destructive TERS analysis, both discoveries can benefit from certain limitations of time interval $\tau_{cont}$ related to time of appropriate tight contact between the tip of the probe and the surface of the sample in each point of chemical analysis. While scanning certain area of the sample, the present invention provides for and benefits from periodic interruption of tight contact between the sharp tip of the probe and the surface of the sample. As a result, each period of the invented methods include: (i) bringing the probe into appropriate contact with one point of the sample, (ii) making chemical analysis of this point during limited time interval $\tau_2$ (which is equal said above contact time $\tau_{cont}$) with the use of TERS procedure, (iii) terminating said contact by increasing the distance between the probe and the sample, and (iv) relocating the probe into another point of the analysis during another time interval $\tau_1$.

It follows logically from what is said in few previous paragraphs that a device of the invention providing non-destructive TERS analysis must comprise at least one additional element 27 depicted in FIG. 8 and FIG. 9 which is capable of producing periodically at least two electric signals associated with at least two time intervals $\tau_1$ and $\tau_2$, said two signals correlated with switching between two different regimes of the device. These two time intervals can be defined electronically, for example with the use of controlling computer 25 or any other means capable of measuring time intervals, and repeated periodically while scanning so that signals associated with time interval $\tau_2$ are used to provide specific regime of SPM operation during interval $\tau_{cont}$ described above. On the other hand signals related to time interval $\tau_1$ may be used to provide another specific regime of SPM operation during an interval $\tau_{reloc}$ required for relocation of the probe to another point of the analysis. It has to be stressed that time interval $\tau_1$ comprises desirably certain additional time which is necessary for preceding safe microscopic exploration of particular point of the sample chosen for current analysis. That is why in most cases at least one signal associated with time interval $\tau_2$ follows desirably after the end of interval $\tau_1$. Both said time intervals may be programmatically predetermined by either user or manufacturer of the device. It should be appreciated by anyone of ordinary skill in the art that this element 27 may be designed technically in different forms and represented by relatively complicated combination of many electronic and/or mechanical elements, including but not limited to software and hardware elements, such as, for example, as internal clock and/or program of computer 25. In any case the element 27 is used for switching behavior of whole device, causing for example switching between different types of a behavior of the scanner 26, namely between two quite different regimes as shown by arrows in FIG. 8 and FIG. 9. That means that settings specific for one regime define details of an operation of SPM during time interval $\tau_1$ corresponding to both $\tau_{reloc}$ and preceding microscopic analysis of chosen point, and different settings specific for another regime define fully changed operation of both the SPM and all components of spectral analysis system (which includes such parts as 5, 6, 7, and 25 described before) during time interval $\tau_2$ corresponding to $\tau_{cont}$. Accordingly to what was said before these two regimes may be quite different in regard of Z-coordinate of the probe relatively sample's surface and the speed S related to changing X-, Y-plane coordinates of the probe. Exemplary technical details of invented method are disclosed herein below.

Because all operations of SPM are performed in real time regime(s) only, and in accordance with time schedule predetermined by time settings made before beginning of scanning, the particular time period of tight contact ($\tau_2$) is set preliminary and corresponds to duration of so-called second regime SPM operation. The time-point of beginning of tight contact may be recorded by feedback system because signals of feedback system depend strongly on the force of interaction between the tip and the sample—the device is Atomic Force Microscope. There is no another way to control the time of real tight contact.

We define "good $\tau_2$" or "acceptable $\tau_2$" if at each surface point this $\tau_2$ is sufficiently long that an amount of scattered light, e.g., the number of quanta collected during $\tau_2$ and transferred to optical spectrometer is enough to produce a record exceeding noise level. Of course, it depends on intensity of laser beam illuminating the tip, capability of collecting optics, and quality of the spectrometer. Our experience based on rather good optical system shows that $\tau_2$ should be at least 0.001 s when the tip is illuminated continuously.

As used herein, the term "acceptably good $\tau_2$" can be made even shorter by at least one order of magnitude for example, of at least about 0.0001 s) if periodically interrupted illumination is used because in this case the instant intensity of illumination can be increased by the order of magnitude without overheating of the tip.

General Structure of Preferred Embodiments

A first (preliminary) step of the non-destructive method of present invention comprises following general features:

Step (a) providing a device comprising a suitably programmed computer, a scanning probe microscope (SPM) operably linked with an optical spectrometer so that said device is capable of following general operations:
  (i) changing position of a probe of said microscope relatively a sample in any of three dimensions;
  (ii) illuminating a sharp tip of said probe with focused laser beam;
  (iii) providing chemical analysis of a substance located on the surface of said sample in proximity of said sharp tip, said analysis based on optical spectrometry of a light emitted from said proximity of said sharp tip;

General operation (i) of preliminary step (a) may be performed in at least two different ways so that the device of the invention is also capable of following additional operations:
  (iv) producing at least two electric signals separated in time and associated with at least two time intervals $\tau_1$ and $\tau_2$, said producing organized so that at least one said signal of said two, namely the signal associated with beginning of second interval $\tau_2$ is produced after the end of said first interval $\tau_1$, and
  (v) periodic programmable switching between at least two different regimes of SPM operation while scanning of sample's surface, said switching synchronized with electric signals produced while operation (iv) mentioned above. In this case said scanning of sample's surface is understood as microscopic measurements done in at least one point of the sample and desirably in more than one point, wherein time interval $\tau_1$ relates to the first regime of said two and the second regime of said two continues for said time interval $\tau_2$.

Another general operation (ii) of preliminary step (a) may be also performed in at least two different ways. In one case the illumination of the sharp tip with focused laser beam can be done continuously with no interruption, whereas in the second case said illumination of the sharp tip may be periodically interrupted so that the sharp tip undergoes laser illumination only during one time interval of said two, for example during time interval $\tau_2$. That means that in such second case the illumination of the sharp tip with focused laser beam is to be activated before beginning of said second regime of SPM operation and terminated after the end of said second regime.

The first case of continuous illumination is more simple technically but it can result in undesirable overheating of the sharp tip 12. At the same time more complicated periodic interruption of the illumination may be quite useful in order to increase sensitivity of the analysis and to prevent overheating of the tip with sharply focused laser beam. It should be appreciated by anyone of ordinary skill in the art that in the second case considered above the device of the invention must be supplied with appropriate system 28 capable of interrupting laser beam 2 focused on the sharp tip of the probe. For simplification of drawings of the invention the optional system 28 is shown in FIG. 12 as simple dashed rectangular. However, it should be appreciated that there are different technical possibilities to design such system 28 with the use of either pure electronic modulator, or opto-electronic modulator, or opto-mechanical approaches. As most simple example of opto-mechanical approach only, the system 28 may include traditional rotating disk optical modulator which has multiple holes and is switching light beam ON-OFF synchronically with periodic repetition of both time intervals $\tau_1$ and $\tau_2$ mentioned above. It should be appreciated that the system 28 must comprise standard technical elements providing synchronization of the modulator with both SPM and the optical spectrometer.

Note that FIG. 12 demonstrates two different options of optical organization of general operation (ii) above, namely either directing the beam 2B through the lens 5 or independent directing the beam 2A. It should be appreciated that a position of said system 28 is shown in FIG. 12 as an example only, and actual position of the system 28 in real device can be chosen so that said modulation of primary laser beam 2 falling onto the tip 12 can be performed in the case of any of said two options of optical organization.

The last general operation (iii) of preliminary step (a) requires the device of the invention to be capable of performing at least following additional operations:
  (vi) collecting a light emitted from proximity of said sharp tip for spectrometric analysis provided by said optical spectrometer;
  (vii) accumulating spectral data provided by said optical spectrometer, said accumulating performed in each point of the sample's surface during such predetermined limited time interval which doesn't exceed time interval of illumination of said sharp tip, for example time interval $\tau_2$; and
  (viii) storing in memory both current coordinates of the probe relatively the sample and results of said spectrometric analysis related to said current coordinates.

It is to be noted that most of technical features (i-viii) of the step (a) are highly desirable for the method of present invention. However it has to be understood that some other technical features of the equipment may be also very desirable due to they can improve performance and deliver additional useful information to users. For example only, the device of the step (a) may be also supplied with a software capable of mapping a distribution of chemical compounds over scanned area of the sample.

Other useful technical features may be included as well. For example, it may be very useful and desirable that at any time moment all three coordinates X, Y, and Z of the probe 18 relatively the sample are measured by corresponding coordinate sensor system 22 providing high precision of such coordinate measurement. It is desirable that SPM used in this invention is capable of programmable relocating the probe 18 relatively the sample with the use of either data of coordinate sensor system 22 or feedback signals created by corresponding feedback system(s). The point (v) above assumes that the SPM of the invention is capable of programmable switching between these two possibilities (actually, between two different regimes) of the operation. Correspondingly, the general point (i) above also assumes that desirable changing position of the probe relatively the sample can be provided in any of said two different regimes.

It also can be desirable that SPM used in this invention is supplied with electronic system 24 capable of exciting oscillation of probe 18 supplied with the needle 11. In some embodiments system 24 can accept a piezoelectric signal produced by deformed probe 18 made as piezoelectric resonator. This 2-way electronic communication between the probe 18 and the system 24 is shown in FIG. 7 as double-directed thick white arrow. The piezoelectric signal created by either "tuning fork" or other type of piezoelectric resonator is usually used as feedback signal for SPM operation while scanning the surface of the sample 1. However, if the probe 18 is represented by traditional cantilever supplied with sharp needle 11 the feedback signal of SPM of the invention is to be created by another system 21 supplied with multi-segment optical detector, said detector participating in so-called "optical lever system" shown in FIG. 7 with dashed arrows 19 and 20 wherein the arrow 19 represents low intensity laser beam focused on a mirror located on free end of the cantilever, and the arrow 20 represents secondary beam reflected by said free end.

Further Operations Based on Step (a)

Non-destructive systems, devices, and methods of the present invention are based on periodic switching between at least two different regimes in each particular point of surface chemical analysis wherein the specific aim of the first regime of said two comprises safe preliminary observation of certain relief parameters of chosen point, and the specific aim of the second regime is safe obtaining of chemical information from that point. That is why the method of present invention provides such new sequence of main steps that both tight contact of the sharp tip 12 of the probe 18 with sample's surface and surface chemical analysis are to be interrupted periodically in correlation with periodic switching between two different regimes of scanning probe microscope, said switching resulting in fully modified trajectory of point-to-point relocation of the probe while scanning. In fact said modified trajectory corresponds in general to hoping from one local surface area of the sample to next one.

It is important to stress that both spatial and time organizations of specific trajectory of such hoping are absolutely different from tapping trajectory of the probe which undergoes oscillating with high frequency about $10^5$ Hz described in previous sections as an example of prior art methods. The point is that in tapping mode (a) the sharp tip 12 of probe never reaches a position of tight contact with sample's surface suitable for TERS measurements, and (b) at high frequency of oscillation the tip 12 spends less than $10^{-6}$ s at lowest trajectory point which is closest to the surface. It may be obvious for a person skilled in the art that even low but any reasonably acceptable sensitivity of TERS measurement requires much longer time.

That is why main peculiarity of present method is that such invented hoping includes both (i) bringing sharp tip 12 of the probe in an appropriate for chemical analysis contact with each local surface point of the sample 1, which is typically a real tight contact in the case of TERS analysis, and (ii) delaying this appropriate contact position of said sharp tip 12 on sample's surface for reasonably chosen time interval $\tau_2$ which is properly long for based on TERS phenomenon chemical analysis of current local surface area of the sample ($\tau_2$ is typically longer or equal 0.0001 s in some embodiments and longer or equal 0.0001 s in other embodiments) and, at the same time, short enough to avoid potential damage to either said tip 12 or the sample 1 ($\tau_2$ is to be shorter or equal 0.2 s by the order of magnitude). That means that in framework of invented method microscopic TERS chemical analysis using optical spectrometry is also to be performed at the time of said delaying, namely for time interval $\tau_2$ limited accordingly to numbers discussed above.

It has to be mentioned that one can use two different approaches to describe basic operations of invented non-destructive method of chemical analysis. The first approach is mainly concentrated on consideration of specific functionality and sequence of operations occurring and repeated periodically at appropriate time intervals. Another approach is mostly based on consideration of spatial organization and specific settings of predetermined parameters of scanning probe microscope corresponding to at least two different regimes of operations of said microscope repeated periodically. It should be appreciated that both approaches are equally important and fully equivalent from viewpoint of final result provided by invented method.

However, now we start to describe most features of the first approach considering different time intervals of sequentially fulfilled operations which are specific for invented method of high resolution and non-destructive microscopic chemical analysis. This approach is based on previously disclosed discovery that tight contact interaction force between the sample 1 and the tip 12 of the probe depends on duration of contact time $\tau_{cont}$. Saying words "tight contact" we mean a contact with so low distance $D_{record}$ between the sample 1 and the tip 12 which is appropriate for chemical analysis with the use of TERS phenomenon. That is why hereinafter the term "appropriate contact" is to be treated as a technical equivalent to words "tight contact". After completing Step (a) described before the method of the invention comprises following general operations:

Step (b) selecting next point of said sample for chemical analysis, said selecting performed during programmatically predetermined time interval $\tau_1$ which is used to provide safe locating the probe 18 over said selected point, said safe locating comprises changing distance between said sharp tip 12 of the probe 18 and a surface of the sample 1;

Step (c) bringing the sharp tip of said probe into appropriate contact with said selected point of the sample located in previous step (b);

Step (d) keeping said appropriate contact during programmatically predetermined limited time interval $\tau_2$ and providing both said illumination of sharp tip 12 with focused laser beam 2 and accumulation of chemical data within the same limited time interval $\tau_2$, said accumulation provided by said optical spectrometry of the light emitted from proximity of said sharp tip 12;

Step (e) terminating said accumulation of chemical data on or before ending of said limited time interval $\tau_2$; and Step (f) returning to the step (b) in order to continue scanning of sample's surface with said SPM or terminating the method if the point analyzed in the step (d) is the last one.

Note that there can be several different ways to perform the step (b) depending on both the program of computer 25 and the state of elements of SPM just before beginning of said step (b). In that regard it has to be noted that the term "next point of said sample" in the step (b) equally relates to either a first point of chemical analysis or any other point of chemical analysis including a second point and all other points. However programmatically determined behavior of SPM may be different in different points and, correspondingly, the step (b) may either include or skip certain sub-steps described below. The only necessary condition is that in the beginning of the step (b) a specific first regime of SPM operation must be initiated, said first regime corresponds to such setting of SPM that while step (b) Z-coordinate of the probe 18 relatively the sample 1 is always chosen to be in accordance with safe high distance $D_{safe}$ discussed before.

If a point selected for chemical analysis is said first point, which has not been analyzed before the SPM switched to said first regime in the beginning of the step (b) performs so-called "landing" sub-step operation, establishes safe $Z_0$-coordinate of the probe 18 relatively the sample 1 which is typically less than preceding Z-coordinate. After that the SPM immediately begins next step (c) so that sub-steps of the step (b) changing X-Y coordinates of the probe 18 relatively the sample 1 are skipped. It has to be stressed that said sub-steps of the step (b) changing X- or Y-coordinates of the probe 18 may be also skipped at least one time and desirably more than one time in any selected point if the computer 25 is programmed to perform chemical analysis of this selected point more than one time.

The initial state of elements of SPM may be quite different in the beginning of the step (b) if chemical analysis of the sample has been performed already at least one time and the method comes again to the step (b) after preceding step (f). This initial situation always takes place before selecting all next points except the first one. In this case initial position of the probe relatively the sample is defined by said second regime initiated in preceding step (c) which provides said appropriate contact relating typically to rather low distance $D_{record}$. Correspondingly, in this case occurring in the step (b) switching SPM from said second regime back to the first regime results in immediate increasing Z-coordinate of the probe relatively the sample and its returning to said safe $Z_0$-coordinate.

However, in most typical cases each selected point of the sample is desirably analyzed only once and the number of such points is more than one. That means that in such typical cases said selecting next point for chemical analysis in step (b) must comprise sub-steps changing either X- or both X- and Y-coordinates of the probe 18 relatively the sample 1 in order to provide safe locating the probe 18 over said next selected point. Due to said first safe regime of SPM operation is always initiated while steps (b) said locating results in safe moving sharp tip 12 along the surface of the sample from previous point to the next one. This X-Y relocation is safe because while step (b) Z-coordinate is always chosen to be safe $Z_0$-coordinate in accordance with safe high distance $D_{safe}$. Predetermined time interval $\tau_1$ is used mainly for both changing said Z-coordinate and said X-Y relocation from one point to next one. It should be appreciated that programmatically determined time interval $\tau_1$ can be made shorter in such points where sub-steps of said X-Y relocation can be skipped programmatically and only Z-change is required.

Next step (c) requires changing of the regime of SPM operation at some moment of the time because, in contrast to regime of the step (b), it provides further Z-relocation of the probe 18 relatively the sample 1. That is why it comprises sub-step of safe microscopic exploring of sample's relief in chosen point, for example with the use of so-called safe tapping mode shown in FIG. 11 as high frequency oscillation of the probe 18 with high amplitude 2×A. This sub-step provides necessary microscopic information and then results in decreasing the distance between the tip 12 and the sample 1 at this chosen point of sample's surface from initial high distance $D_{safe}$ (see FIG. 11) to such low distance $D_{record}$ (see FIG. 12) which is appropriate for chemical analysis. Both step (b) and mentioned above sub-step of the step (c) may be performed in the very end of same time interval $\tau_1$ corresponding to the first regime of SPM operations. However the said above may mean that the first regime of SPM operation comprises at least two sub-regimes, namely the sub-regime of X-Y relocation and the sub-regime of microscopic exploring preceding final Z-relocation of the probe. At the same time it should be appreciated that final part of Z-relocation performed in the step (c) and resulting in much lower distance $D_{record}$ (see FIG. 12) requires switching from first regime of SPM operation to the second one which must be done out of interval $\tau_1$. That is why said final part of the step (c) may be included into very beginning of next time interval $\tau_2$. At the same time it should be appreciated by anyone of ordinary skill in the art that in some embodiments of the invention a creation of at least one electric signal initiating switching from a first regime of SPM operation acting while step (b) to a second regime of SPM operation acting while step (d) can be performed in framework of the step (b) whereas in another embodiments both a creation of similar electric signal and transition from the first said regime to said second one can be performed in framework of next step (c).

The change of the Z-distance during step (c) described above may include optional sub-step which comprises keeping a focus of laser beam 2A on moving sharp tip 12 (see FIG. 12). It can be appreciated that this sub-step is useful for automatic operation and becomes possible when the device of the invention comprises certain automatically operated mechanism which is connected with optic elements providing focused illumination of the tip 12. For example only this focus keeping mechanism may be represented by piezoelectric scanner 29 connected with controlling computer 25. Such scanner 29 (not shown in FIG. 11 and FIG. 12 for simplification of drawings) is capable of moving focus point of laser beam 2A concentrated on the sharp tip 12 synchronously with spatial relocation of the needle 11. In other optional embodiments considered later in more details similar scanning mechanism 30 may be connected with lens 5 in order to control focus point of laser beam 2B shown in FIG. 12. It should be appreciated that either presence or absence of said scanners 29 and 30 are just technical options which do not change main scope of present invention at all but may improve technical characteristics when necessary or desirable.

A difference between: (a) such scanners 29 and 30 used for improved chemical analysis by means controlling direction of primary laser beam 2 and position of its focus point, and (b) optional laser beam 19 discussed previously as traditional elements of optical lever system creating feedback signals used for SPM operation.

In the step (d) disclosed above limited time interval $\tau_2$ relates to duration of another (namely, second) regime of SPM which coincides with programmatically predetermined desirable time interval $\tau_{cont}$ of tight contact discussed above. That means that the step (d) may comprise sub-step of switching from the first to the second regime of SPM operation if such switching is not performed in either step (b) or (c). Limitation of $\tau_{cont}=\tau_2$ is necessary to prevent development of growing in time too high interaction force between the sample 1 and sharp tip 12 when the tip is brought to rather low distance $D_{record}$. It was discovered by authors and disclosed in present specification before that in any case it is desirable that $\tau_{cont}$ (and corresponding $\tau_2=\tau_{cont}$ which defines duration of the step (d)) is less than 0.2 s by the order of magnitude, more desirably is less than 0.05 s, and even most desirable $\tau_{cont}$ is in between 0.01 s and 0.001 s. In certain embodiments of the invention providing high instant intensity of focused laser beam 2 the range of most desirable $\tau_{cont}$ can be expanded to be in between 0.01 s and 0.0001 s. Fulfilling of these numeric limitations by proper choice of time interval $\tau_2=\tau_{cont}$ avoids potential damage to either tip 12 or the sample 1 or both because technical time interval $\tau_2$ of duration of second regime creates practically the same limitation of actual contact time $\tau_{cont}$.

It can be appreciated by anyone of ordinary skill in the art that for proper chemical analysis using TERS phenomenon at current surface point, both laser illumination of the sharp tip 12 and said appropriate tight contact corresponding to low distance $D_{record}$ must be kept during appropriately chosen time interval $\tau_2$ of the step (d) for simultaneous accumulation of chemical data provided by optical spectrometry of the light emitted from proximity of the sharp tip 12.

It can also be appreciated that the step (d) can comprise an optional sub-step of switching back from the second regime of SPM operation to the first one in order to interrupt said tight contact when time interval $\tau_2$ is over. This option is to be used if said switching back is not done in the beginning of the step (b) as disclosed before.

In some embodiments of the invention said optional sub-step of the step (d) comprises creating another electric signal on of before very end of time interval $\tau_2$, said another electric signal used for initiating said switching back for returning to the first regime of SPM operation and also for terminating said accumulation of chemical data while next step (e).

It follows from what has been said before and can be appreciated that said illumination of the tip 12 is useful for chemical analysis only during such time interval(s), namely the interval $\tau_2$, when a distance between the sample and the tip 12 is low enough and corresponds to appropriate $D_{record}$. During all other time intervals this illumination is useless. That is why in some simplified embodiments of the invention the illumination of the tip 12 may be provided continuously but used only while interval $\tau_2$ of the step (d). At the same time in some a little bit more complicated embodiments of the invention the illumination of sharp tip 12 may be activated just before the step (d), namely while step (c) at either very beginning of time interval $\tau_2$ or very end of time interval $\tau_1$. In this case it should be appreciated also that said illumination of the sharp tip with focused laser beam is to be periodically terminated before returning to next step (b). It should be clear that such periodic activation and termination of said illumination prevents overheating of sharp tip 12 by focused laser beam and may result in increased sensitivity of chemical TERS analysis.

One more optional sub-step may be employed at either end of the step (c) or between steps (d) and (e), and in any case not later than in just beginning of the time interval $\tau_2$ of the step (d). This sub-step may prevent scratching of sample's surface by sharp tip 12 brought in tight contact with the sample. This prevention results from establishing such safe speed $S_2$ of the scanner 26 moving either the sample 1 or the probe 18 in X-Y plane that during limited time interval $\tau_2$ shift of the tip 12 in X-Y plane is so low that their product $S_2\tau_2$ doesn't exceed 3 nm, and more desirably $S_2\tau_2$ doesn't exceed 1 nm. In certain special cases it may be desirable that said speed $S_2$ is kept equal zero during limited time interval $\tau_2$ in order to obtain both highest possible spatial resolution of microscopic chemical analysis and to avoid both even low possibility of sample's scratching and/or either deformation or break of the sharp tip 12.

At the same time it can be appreciated by anyone of ordinary skill in the art that it makes no sense to keep so low $S_2$ after termination of the step (d). That is why it may be recommended in present invention that either step (e) or step (f) comprise optional sub-step changing the speed of movement of probe 18 along X-Y plane of sample's surface from the value $S_2$ kept during the step (d) to another value $S_1$ exceeding said $S_2$ so that relocating of the probe during next step (b) takes as short time as desired. Such regime of SPM operation resulting in periodic switching between said speed $S_1$ and said speed $S_2$ is demonstrated in FIG. 10.

It has been previously mentioned in this specification that proximity of the sharp tip 12 emitting secondary light has extremely low volume. That means that sensitivity of the method invented depends greatly on whether light collecting optics is well focused on said proximity or not. Taking this into account it may be noted that in framework of the same scope of the invention the sensitivity of present method of chemical analysis can be highly improved if the device of the invention comprises optional automatically operated piezoelectric scanner 30 capable of controlling position of focus point of at least one optic element 5 in order to keep this focus point on said proximity of the sharp tip 12 (see FIG. 12). An advantage of using piezoelectric scanner 30 in an optical channel of secondary emitted light is that position of focus point of light collecting optic element(s) can be automatically adjusted on proximity of the sharp tip 12 with precision about few nanometers independently on spatial relocations of the probe 18. It should be appreciated that such automatic adjustment becomes possible when the scanner 30 is operably linked with the same controlling computer 25 which coordinates operations of both scanning probe microscope and optical spectrometer used for chemical analysis of emitted light.

Now we are going to discuss an invented method from viewpoint of another approach which is mostly concentrated on important specific spatial characteristics of different regimes related to SPM operations, rather than organization of these operations in time. By the term, "different regimes" of SPM operations, we mean that in each regime a behavior of a device is based on specific settings stored in computer's memory. Any change of said settings can cause the change of said regime of operation.

For example, one setting (and correspondingly one regime) may relate to predetermined feedback signal, and SPM behaves so that said feedback signal is kept in predetermined technical brackets. In this case coordinate sensor system(s) 22 play the role of passive recording elements providing coordinate information to controlling computer 25. Feedback signal(s) may relate to high frequency oscillation of the probe 18, or to phase shift of these oscillation relatively exciting voltage of the system 24, or to doubled amplitude 2×A of said oscillation (see FIG. 11).

As an example of another regime, the setting may relate to predetermined deformation of the probe 18, said deformation resulting from the interaction of sharp tip 12 of the probe with the sample 1. Keeping predetermined deformation is based on signals sent to computer 25 by either system 24 explained before or by optical detector system 21. In this case all previous parameters related to oscillation of the probe become passive and do not influence behavior of SPM even if they are recorded by controlling computer.

One more different regime is available if coordinate setting becomes dominant programmatically. In this case controlling computer operates predetermined Z-relocation of the probe on the basis of data obtained from coordinate sensor system 22. At the same time all other parameters play only passive information role which doesn't influence the behavior of SPM.

The said above in three previous paragraphs can be taken into account for better understanding of the information provided below. In order to achieve specific advantages related to non-destructive and well reproducible chemical analysis of the surface, the method of present invention comprises following main steps repeated periodically.

First, a general set of steps is represented below to demonstrate operations involved. However, in different embodiments each particular step may be performed with the use of different technical details, or may include some additional sub-steps. These additional details will be disclosed later. We need not repeat the Step (a) related to technical features of the device described in previous sections, and concentrate here on characteristics of operations performed by this device. Thus, a general set of said operational steps can be represented by the following steps.

Step (b). Initiating a first regime of said SPM, comprising for example so-called intermittent contact regime in which controllable relocation of the probe along sample's surface is safe, whereas damages of both the tip and the sample are fully prevented by permanent keeping at least a predetermined minimum safe distance $D_{safe}$ between said sharp tip 12 and a surface of the sample 1. Specific settings of SPM in the first regime may be different but in any case conditions of previous sentence must be satisfied. As an example only and for better understanding of intermittent contact regime, FIG. 11 depicts high frequency Z-oscillation of the probe 18 together with its needle 11 over the surface of the sample 1. Obviously, in this case the distance between the tip 12 and the surface of the sample 1 changes quickly so that the upper and lower positions of the needle and its tip 12 are shown in FIG. 11 with dashed lines. However, even said lower position of the tip 12 corresponds to said minimum safe distance $D_{safe}$. In the first regime the SPM keeps predetermined value of feedback signal resulting from said Z-oscillation. That means that current setting of feedback signal related to the first regime of SPM reflects at least one physical parameter of said oscillation. In this regime the feedback signal provided by either system 24 or system 21 may relate to either frequency (typically in between 50 KHz and 1 MHz), or its phase, or doubled amplitude of oscillations 2×A as discussed before. Note that in the first regime different feedback signals may be set programmatically in different periods if necessary or desirable.

Step (c). Selecting programmatically next desirable point of the sample to be analyzed and positioning said sharp tip 12 over said next point, said positioning results from both moving either the probe 18 or the sample 1 in X-Y plane, which is substantially parallel to sample's surface and simultaneous establishing such $Z_0$-position of the probe relatively the sample, which provides at least said minimum distance $D_{safe}$ in proximity of said next desirable point accordingly to said first regime of the step (b). Note that due to unpredictable relief of the surface $Z_0$-positions may be different in different points of analysis (for example, compare different positions of the needle 11 in two points A and B in FIG. 9). Note also that in some periods the step (c) may be skipped for programmatically predetermined number of full cycles of the method if there is a need to repeat surface analysis in the same surface point more than one time.

Note that in some embodiments the step (c) may comprise a sub-step forming a numeric value of $Z_0$-position established in the step (c) and memorizing this numeric value by sending it to a memory of controlling electronics, for example a memory of controlling computer 25. Specific numeric value of $Z_0$-position is formed by coordinate sensor system 22 (see FIG. 11) in each surface point of the sample which is chosen for the analysis in framework of activity of said first regime. Said numeric value of $Z_0$-position is an important spatial characteristics which represents quantitatively $Z_0$-coordinate of the probe relatively either the sample 1 or stable base 23 of SPM, said $Z_0$-coordinate resulting from safe locating of the probe over said next selected point.

Step (d). Switching SPM programmatically from said first regime to a second regime by changing at least one setting parameter of SPM operation. In some embodiments of present invention said change of at least one setting parameter may relate to change of either predetermined value of feedback signal or physical nature of feedback signal. Only as one of many possible examples of such change of physical nature, the initial feedback signal created by either the system 24 or the system 21 and reflecting physical parameters of oscillation of sharp tip of the probe 18 (see FIG. 11) may be changed to quite different feedback signal created, for example, by opto-electronic system 21 and reflecting static deformation of the probe 18 as depicted in FIG. 12 wherein said deformation causes light beam 20 to change direction from 20A to 20B. It should be appreciated that such static deformation of the probe 18 (provided here as an example only) either suppresses or excludes completely any high frequency oscillation of said sharp tip. In other embodiments said change of setting parameter may relate to a system operating with signals of at least one coordinate sensor system 22 associated with Z-position of the probe. This kind of embodiments (discussed later in the section called Example #2) requires memorizing $Z_0$-position established in step (c) in the memory of controlling computer 25. Note that programmatic switching between two regimes in the step (d) may comprise a sub-step initiating a system controlling a duration $\tau_2$ of said second regime in time for its proper termination when programmatically predetermined time interval $\tau_2$ expires.

Step (e). Moving either the sample or the probe in Z-direction for changing Z-position of the probe 18 using SPM operation in said second regime so that the tip 12 of the probe gets a new Z-position which is more appropriate for desirable type of chemical analysis than previously found $Z_0$-position. It should be appreciated that desirable type of chemical analysis may be either a tip enhanced Raman scattering of the light emitted from proximity of said sharp tip 12, or tip enhanced laser-induced fluorescence in chosen point, or other type. It is desirable also that the new Z-position satisfies following programmatically predetermined conditions:

(i) the new Z-position=$Z_0$-position+$\Delta Z$, wherein $\Delta Z$ is separately determined parameter, and (ii) the new Z-position results in establishing new distance $D_{record}$ between the tip 12 and the surface of the sample 1, said new distance $D_{record}$ creates no damage to both the sharp tip 12 and the sample 1 when this new distance $D_{record}$ is kept for predetermined limited time interval of the contact $\tau_{cont}$ (determination of this interval $\tau_{cont}$ has been discussed before). It should be appreciated that this limitation in time of both said $\tau_{cont}$ and new distance $D_{record}$ obtained in the second regime leads logically to a condition that the second regime of SPM operation can continue only for limited time interval $\tau_2$ which is close or desirably equivalent to said $\tau_{cont}$. The second regime must be terminated later when the interval $\tau_2$ expires. Desirable numeric values of $\tau_2$ have been disclosed before.

In some cases depending on both the nature of the sample, material of the tip 12, and desirable type of chemical analysis said new Z-position may correspond to decreased distance $D_{record}<D_{safe}$ between the tip 12 and sample's surface. In other, relatively rare cases, new Z-position may relate to increased distance $D_{record}>D_{safe}$ between these two elements. Determination of optimum parameter $\Delta Z$ as far as technical details and elements involved in said changing Z-position of the probe may be different in different embodiments and will be discussed separately herein below.

Step (f). Illuminating said sharp tip 12 of said probe 18 with focused laser beam 2. In some embodiments this illumination may be initiated by corresponding sub-step performed at any time point between preliminary step (a) and the next step (g). If the laser 4 produces non-interrupted continuous laser beam 2, the initiation of the illumination can be done only one time while the first period of the method with no repeating said initiation in other periods. In this case the only important condition is that the tip 12 must be illuminated by laser beam 2 during next steps (h, i) and said sub-step initiating this illumination is performed before the step (g). In other embodiments said illuminating may be interrupted periodically in order to prevent overheating of the probe. In these cases the sub-step initiating said illuminating must be performed just before each step (g), and the illumination is to be terminated at any moment after step (i) and before returning to step (b) provided by the step (k).

Step (g). Collecting the light 9 emitted from proximity of said sharp tip 12, said collecting provided by optical system 5 and aimed to direct the emitted light onto an entrance of optical spectrometer 6.

Step (h). Initiating data recording, said data obtained from spectrometric analysis of said emitted light by said optical spectrometer 6, said recording continuing for a predetermined time interval $\tau_{record}$ which cannot exceed said time interval $\tau_2$ limiting a duration of said second regime and desirably doesn't exceed the predetermined limited time interval of the contact $\tau_{cont}$ which is close or equivalent to $\tau_2$.

Step (i). Interrupting data recording, namely said data recording related to present point of surface chemical analysis, said interrupting performed at the moment of expiration of said predetermined time interval $\tau_{record}$ which is on or before of the end of predetermined limited time interval $\tau_2$.

Step (j). Storing data accumulated during step (i) in memory of controlling computer 25 so that said record is associated with stored X and Y coordinates of the probe 18, said X and Y coordinates correspond to the current point of analysis. The data obtained contain the information related to chemical compounds located on the surface in present selected point.

Step (k). Terminating the method if the present selected point of chemical analysis is the last one. Otherwise returning to step (b) in which operation of SPM (i) comprises automatic termination of said second regime at the end of said time interval $\tau_2$ by changing at least one setting parameter, and (ii) will be switched again to the first regime in order to relocate the probe 18 safely to the next desired point of the surface of the sample 1. In this case the device of the invention repeats the sequence of steps (c) to (k) for surface chemical analysis of the next desirable point.

This step (k) provides periodicity of the method of present invention and means returning to safe $Z_0$-position of the probe which reduces the chances of damage while traveling of the probe along main XY surface plane of the sample.

It can be appreciated that general methods of present invention described above solves the problem of prior art methods. The new methods of this invention substantially decrease the chances of causing damage to either the probe or the sample. Particularly the invented new method eliminates the combination of prior art operations in which non-interrupted too tight direct contact (either electric or mechanical one) of the probe with the surface of solid sample occurs simultaneously with continuous movement of said probe along the surface.

EXAMPLES

The following examples illustrate some specific embodiments of the invention. These examples are not intended to limit the scope of the invention, and based on the general descriptions above and the specific descriptions in these examples, persons of ordinary skill can readily create additional embodiments. All of those embodiments are considered part of the invention.

The general methods disclosed in previous section is fully applicable to all embodiments of present invention. However, some specific details of different embodiments may be different as well.

There are two main versions of embodiments of the invention in which different technical approaches are used to provide steps (d) and (e) in order to switch regimes of SPM and cause desirable transition from relatively high $D_{safe}$ to relatively low (in most cases) $D_{record} < D_{safe}$. For simplicity and better understanding of said difference it would be easier to think that in both said versions initial $D_{safe}$ is to be established with the use of the same first regime of SPM operation described in the steps (b) and (c) of general method, namely the regime of intermittent contact wherein the probe 18 oscillates with high frequency and predetermined by chosen setting feedback signal relates to at least one of few measurable parameters of this oscillation.

In the version #1 electronic system 24 excites high frequency oscillation of the probe 18 and simultaneously the same system 24 may be used as the source of feedback signals in the case if the probe 18 is attached to piezoelectric resonator. In the version #2 opto-electronic system 21 may be used as the source of feedback signals in the case if the probe 18 is attached to traditional cantilever. Given that one should only consider how different are these two versions in regard of steps (d) and (e).

Example 1

In this example, settings of SPM are switched programmatically in the step (d) so that the operation of SPM changes from the first regime to the second one. In any case that should result in setting of another predetermined feedback parameter which is different from that in the first regime. The result provided by the step (f) is that the probe 18 and its tip 12 are shifted relatively the sample in Z-direction closer to the surface of the sample 1 until predetermined static deformation of the probe 18 is reached. That is how the contact between the sample and the tip 12 is established in the step (e) in accordance with desirable lower distance $D_{record}$ shown in FIG. 12. During the second regime new distance $D_{record}$ is fixed because Z-operation of SPM is built so that Z-coordinate of the probe 18 is defined by stable feedback signal of second regime coming to controlling computer 25 from either system 21 or system 24. Thus, in the embodiments of this example, the feedback system remains active in the second regime, namely during all steps from (e) to (i) inclusively. At the same time, in second regime mentioned stability of $D_{record}$ provides stable tight contact which means that high frequency oscillation of the tip 12 is practically fully suppressed. That is why said oscillation should not be excited by the system 24 in the second regime.

Example 2

A difference in this example from that in Example 1 is that in this example, settings of SPM are switched programmatically in the step (d) so that feedback system controlling Z-position of the probe 18 becomes fully disconnected from scanning mechanism 26 and disabled temporarily while all steps from (d) to (i) inclusively. Thus, Z-movement of the probe 18 relatively the sample 1 during step (e) occurs in accordance with predetermined change of readings of a coordinate sensor system 22 only, so that predetermined value $\Delta Z$ is reached which results in transition of numeric values reflecting position of the probe 18 relatively the sample 1 from initial safe $Z_0$-position to new Z-position and corresponding change of the distance from initial $D_{safe}$ to appropriate for recording distance $D_{record}$. In that regard it can be noted that predetermined value $\Delta Z$ used in embodiments of this Example 2, may be defined and optimized with the help of few separate preliminary measurements provided in ether one or more points of given particular sample before starting scanning of full sample area.

One more difference between the two examples is that at certain $\Delta Z$ values in Example 2 allows keeping needle 11 oscillating slightly with both high frequency and controllable amplitude if the system 24 is not disabled in the second regime.

It can be noted also that in both Example 1 and Example 2, methods of the invention may include additional TERS measurements performed at any appropriate moment when the distance between the tip 12 and the sample 1 exceeds desirable contact distance $D_{record}$. Such additional measurements can be included into the set of general steps described above as additional steps in order to control chemical purity of the needle 11 and, if necessary, in order to increase precision of chemical analysis of the sample by subtraction of chemical contaminations located on the needle.

Example 3

In this example we compare technical abilities related to two different embodiments of invented method wherein an embodiment #1 uses continuous illumination of sharp tip 12 with focused laser beam and an embodiment #2 uses periodically interrupted illumination of the same tip.

Embodiment #1 Having Continuous Illumination

It may be desired that the device of the invention is analyzing the area of the sample 1×1 square micron with resolution 200×200 points and typical constant laser illumination 0.0001 W applied to the area of sharp tip 12 about 0.2 square micron which corresponds to mean intensity of said illumination about $5 \times 10^4$ W/cm$^2$ resulting in acceptably low heating of said tip.

Such conditions mentioned above require collecting secondary light 9 and accumulation of chemical information provided by optical spectrometer 6 for limited time interval $\tau_2$ at least 0.004 s in each point of chemical analysis (steps from (d) to (j)). In the case of TERS analysis the time $\tau_2$=0.004 s corresponds to the time of tight contact discussed before. It also requires time $\tau_1$ about 0.001 s for relocating of the tip from one point of sample's surface to the next one. As a result the device of embodiment #1 must spend at least 0.005 s in each surface point so that full time of scanning desired area of the sample cannot be less than 200 s.

Embodiment #2 Having Periodically Interrupted Illumination

The device of this embodiment is supplied with simple system 28 capable of periodic interruption of focused laser beam 2. This system comprises a disk modulator having 40 openings and rotating with low frequency 1200 turns/min so that interruption of the beam 2 occurs with a period 0.00125 s. In that period only 0.00025 s is used for illumination of the tip 12, and remaining time 0.001 s corresponds to non-illuminated tip 12.

It has to be appreciated that at such conditions the intensity of the beam produced by the laser 4 and falling onto the disk of said system 28 may be increased by the factor 16. The result is that due to shortened illumination time $\tau_2$ the mean intensity of illumination of the tip 12 doesn't differ from that in embodiment #1, and, correspondingly, there is no practical change of the heating of the tip.

At the same time instant intensity of illumination of the tip becomes about $8 \times 10^5$ W/cm$^2$ in short time intervals $\tau_2$=0.00025 s which now can be used as shortened contact time.

Correspondingly, intensity of the light emitted from proximity of the tip 12 increases 16 times as well, and the embodiment #2 can accumulate the same amount of chemical information in 0.00025 s as the embodiment #1 in longer time 0.004 s. However, taking into account that transition from one point to the next one takes about the same $\tau_1$=0.001 s the time spent by the device of embodiment #2 for the analysis of one point is shorter 4 times in comparison with the time spent by embodiment #1. Actually this means that embodiment #2 fulfills the same task in as short time as just 50 s which is 4 times faster than embodiment #1.

Example 4

In this example, one more additional step may be desirable, namely the step of chemical mapping of full area scanned by SPM in framework of the method of present invention. This step is based on transfer of chemical information obtained while scanning in each point of surface analysis with known and memorized plane coordinates X-Y. For example, different chemical information mentioned may be represented by different colors or by any other way convenient for visual representation. This step becomes possible if the number of points analyzed exceeds one, and more desirable this number represents plurality of points analyzed, said plurality exceeding one at least one order of magnitude. Additional step of chemical mapping may be extremely useful because it results in visualization of distribution of different chemical compounds over scanned area. This additional mapping step may be performed either point-by-point in the end of each period of the method after the step (1) or after complete termination of the method.

Advantages of the Invention

Advantages of the systems, devices, and methods of the present invention have been already described before in different sections of the present specification. Substantial additional advantages are characteristic of this invention. Moreover, some details of advantages can be expressed numerically. These advantages include the following:

1. The methods disclosed above are practically non-destructive. This is demonstrated by high reproducibility of results of chemical analysis obtained in few (at least three) subsequent scanning of the same sample.

2. The methods disclosed above demonstrate very high spatial resolution in determining of different chemical compounds. This resolution may be as good as about 3 nm.

3. The method disclosed above demonstrates very high sensitivity which corresponds to detection and chemical characterization of single organic molecules located on the surface of a sample. If area of full scan is 200×200 nm the said sensitivity corresponds to detection of about 0.00025 monolayer.

4. The method and devices disclosed above demonstrate an ability to produce desirable chemical information much faster than prior art method and devices, said ability combined with simultaneous keeping all other advantages listed in points 1-3 above.

It can be appreciated by anyone of ordinary skill in the art that the new systems, devices and methods of surface chemical analysis based on TERS phenomenon has been described in present specification as example only. Actually the same method may be easily modified for measurement of other optical characteristics of a surface layer, said characteristics related to chemical nature of compounds located on the surface. These other characteristics may be for example laser-induced luminescence, attenuated polarization, etc. In these cases the only change of the method is required that optical device of preliminary step (a) is to be adapted for recording said other physical parameters of secondary light emitted from proximity of sharp tip 12 of the needle 11.

We claim:

1. A non-destructive method of surface chemical analysis of a sample having a surface, the method comprising the following steps:
   (a) providing a device comprising a programmed computer, and a scanning probe microscope operably linked with an optical spectrometer so that said device is capable of following general operations:
      (i) changing position of a probe of said microscope relative to the sample in any of three dimensions, said probe operably linked to a coordinate sensor system, said coordinate sensor system comprising a feedback sensor capable of producing a signal in response to deformation of said probe and transmitting said signal to said programmable computer;
      (ii) illuminating a tip of said probe with a focused laser beam;
      (iii) providing chemical analysis of a substance located on a first location on the surface of said sample in proximity of said tip, said step of providing comprising illuminating said tip with a focused laser beam and accumulation of chemical data, wherein said analysis is based on optical spectrometry of light emitted from said proximity of said tip;
   (b) selecting a first point on the surface of a sample;
   (c) bringing the tip of said probe into contact with said first point at a pressure of less than $10^6$ N/cm$^2$;
   (d) illuminating said tip for a contact period of time $\tau_{cont}$ with a focused laser beam and accumulating light emitted from said surface, and analysis of chemical data within a time interval $\tau_2$, said accumulating provided by optical spectrometry of the light emitted from the proximity of said tip;
   (e) terminating said accumulation of chemical data on or before ending of said limited time contact period $\tau_{cont}$;
   (f) selecting another point on the surface of said sample for chemical analysis, said selecting performed during a programmatically predetermined time interval $\tau_1$ comprises both changing distance of the probe relative to the surface of the sample in a Z-direction and further locating said probe over said another selected point, said step of locating comprising moving either the probe or the sample parallel to the sample's surface, said moving performed in either of an X or Y direction at speed $S_1$;
   (g) bringing the tip of said probe into contact with said selected point of the sample located in previous step (b), said bringing comprising another step of changing the distance of between said tip of the probe relative to said surface of the sample in the Z-direction;
   (h) keeping said contact during the programmatically predetermined limited time interval $\tau_2$ and illuminating said tip with another focused laser beam and accumulating light emitted from said surface, and analysis of chemical data within said time interval $\tau_2$, said accumulating provided by optical spectrometry of the light emitted from the proximity of said tip;
   (i) terminating said accumulation of chemical data on or before ending of said limited time interval $\tau_2$;
   (j) if said feedback sensor produces a signal indicating probe deformation force of greater than $10^6$ N/cm$^2$, said moving in step (f) in the X or Y dimension is terminated, or said probe is moved away from said surface to reduce said deformation pressure to below $10^6$ N/cm$^2$; and
   (k) returning to step (f) at least one additional time in order to continue chemical analysis for a next selected point of the sample or terminating the method if the point analyzed in the step (h) is the last one.

2. The method of claim 1, said step of changing the distance of the probe relative to the surface of the sample in the step (f) comprises decreasing said distance in the Z-direction when the step (f) is initiated a first time after the step (d), whereas said changing distance of the probe relative to a surface of the sample in step (f) also comprises increasing said distance in the Z-direction if the method returns to step (f) after the step (j).

3. The method of claim 1, wherein step (d) continuously illuminating the tip of the probe with said focused laser beam, said illumination initiated at any time point before first beginning of the step (f).

4. The method of claim 3, wherein said time interval $\tau_2$ doesn't exceed 0.2 s by an order of magnitude, or $\tau_2$ is less than or equal to 0.05 s, or $\tau_2$ is in between 0.01 s and 0.001 s.

5. The method of claim 1, said method of the step (d) further comprising the step of periodically interrupting said laser illumination of said tip so that said illumination takes place only during a limited time interval $\tau_2$ initiated by a signal associated with the beginning of the second interval $\tau_2$.

6. The method of claim 5, wherein said time interval $\tau_2$ doesn't exceed 0.2 s by an order of magnitude, or $\tau_2$ is less than or equal to 0.05 s, or $\tau_2$ is in between 0.01 s and 0.0001 s.

7. The method of claim 5, wherein step (i) further comprises the sub-step initiated by an electric signal associated with the beginning of the first interval $\tau_1$, to terminate said illumination.

8. The method of claim 1, wherein step (h) further comprises moving either the probe or the sample parallel to said sample's surface in either an X or Y direction at a predetermined speed $S_2$ which doesn't exceed speed $S_1$ of similar movement during step (f) and $S_2$ is established so that the product of multiplication $\tau_2 S_2$ doesn't exceed 3 nm, or $\tau_2 S_2$ doesn't exceed 1 nm.

9. The method of claim 8, wherein speed $S_2$ is equal to zero during step (h).

10. The method of claim 8, wherein either step (i) or step (k) further comprises a sub-step of returning said speed of motion from the value $S_2$ to the previous value $S_1$ established in step (f), wherein said previous value $S_1$ is greater than or equal to $S_2$.

11. A non-destructive method of surface chemical analysis of a sample having a surface, the method comprising the following steps:
   (a) providing a device comprising a programmed computer, and a scanning probe microscope operably linked with an optical spectrometer so that said device is capable of following general operations:
      (i) changing position of a probe of said microscope relative to the sample in any of three dimensions;
      (ii) illuminating a tip of said probe with a focused laser beam;

(iii) providing chemical analysis of a substance located on a first location on the surface of said sample in proximity of said tip, said step of providing comprising illuminating said tip with a focused laser beam and accumulation of chemical data, wherein said analysis is based on optical spectrometry of light emitted from said proximity of said tip;

(b) selecting a first point on a surface of a sample;

(c) bringing the tip of said probe into contact with said first point at a pressure of less than $10^6$ N/cm$^2$;

(d) illuminating said tip for a contact period of time $\tau_{cont}$ with a focused laser beam and accumulating light emitted from said surface, and analysis of chemical data within a time interval $\tau_2$, said accumulating provided by optical spectrometry of the light emitted from the proximity of said tip;

(e) terminating said accumulation of chemical data on or before ending of said limited time contact period $\tau_{cont}$;

(f) selecting another point on the surface of said sample for chemical analysis, said selecting performed during a programmatically predetermined time interval $\tau_1$ comprises both changing distance of the probe relative to the surface of the sample in a Z-direction and further locating said probe over said another selected point, said step of locating comprising moving either the probe or the sample parallel to the sample's surface, said moving performed in either of an X or Y direction at speed $S_1$;

(g) bringing the tip of said probe into contact with said selected point of the sample located in previous step (f), said bringing comprising another step of changing the distance between said tip of the probe relative to said surface of the sample in the Z-direction and further comprising the sub-step of initiating said switching from said first regime of the microscope operation to said second regime, said switching initiated by an electric signal performed at very end of time interval $\tau_1$;

(h) keeping said contact during the programmatically predetermined limited time interval $\tau_2$ and illuminating said tip with another focused laser beam and accumulating light emitted from said surface, and analysis of chemical data within said time interval $\tau_2$, said accumulating provided by optical spectrometry of the light emitted from the proximity of said tip;

(i) terminating said accumulation of chemical data on or before ending of said limited time interval $\tau_2$; and (j) returning to step (f) at least one additional time in order to continue chemical analysis for a next selected point of the sample or terminating the method if the point analyzed in the step (h) is the last one.

12. The method of claim 11, wherein said switching results from a programmatically predetermined change of at least one setting of said scanning probe microscope.

13. The method of claim 11, wherein step (h) further comprises the sub-step using an electric signal associated with beginning of the first interval $\tau_1$, to initiate switching from said second regime of microscope operation to said first regime of microscope operation.

\* \* \* \* \*